US012672848B2

(12) United States Patent
Sweeney

(10) Patent No.: US 12,672,848 B2
(45) Date of Patent: Jul. 7, 2026

(54) DIALYSIS CATHETERS WITH INTEGRATED FLUID STATUS SENSING AND RELATED SYSTEMS AND METHODS

(71) Applicant: Foundry Innovation & Research 1, Ltd., Dublin (IE)

(72) Inventor: Fiachra Sweeney, Dublin (IE)

(73) Assignee: Foundry Innovation & Research 1, Ltd., Dublin (IE)

( * ) Notice: Subject to any disclaimer, the term of this patent is extended or adjusted under 35 U.S.C. 154(b) by 1363 days.

(21) Appl. No.: 17/413,856

(22) PCT Filed: Dec. 11, 2019

(86) PCT No.: PCT/IB2019/060669
§ 371 (c)(1),
(2) Date: Jun. 14, 2021

(87) PCT Pub. No.: WO2020/121221
PCT Pub. Date: Jun. 18, 2020

(65) Prior Publication Data
US 2022/0061804 A1    Mar. 3, 2022

Related U.S. Application Data

(63) Continuation-in-part of application No. 15/750,100, filed on Feb. 2, 2018, now Pat. No. 11,039,813.
(Continued)

(51) Int. Cl.
*A61B 8/04*        (2006.01)
*A61B 5/00*        (2006.01)
(Continued)

(52) U.S. Cl.
CPC ............ *A61B 8/445* (2013.01); *A61B 5/1076* (2013.01); *A61B 5/6855* (2013.01);
(Continued)

(58) Field of Classification Search
CPC ..... A61B 8/445; A61B 5/1076; A61B 5/6855; A61B 5/6859; A61B 5/6882; A61B 8/04;
(Continued)

(56) References Cited

U.S. PATENT DOCUMENTS

| | | | |
|---|---|---|---|
| 952,161 | A | 3/1910 | Whyte |
| 1,184,912 | A | 5/1916 | Armitage |

(Continued)

FOREIGN PATENT DOCUMENTS

| | | | |
|---|---|---|---|
| AU | 2013206194 B2 | 4/2015 | |
| CN | 108712880 A | 10/2018 | |

(Continued)

OTHER PUBLICATIONS

International Search Report and Written Opinion dated Feb. 27, 2020, in connection with PCT/IB2019/060669 filed Dec. 11, 2019.
(Continued)

*Primary Examiner* — Eric J Messersmith
(74) *Attorney, Agent, or Firm* — Downs Rachlin Martin PLLC

(57) ABSTRACT

A dialysis catheter with an elongate body has a distal end defining blood removal and return ports communicating with internal blood removal and return lumens extending through the elongate body. A sensing pathway is disposed in or on the elongate body. A vascular dimension sensor is provided to dynamically measure changes in dimension of the SVC or IVC during dialysis. The sensor communicates with a control system and may be controlled or positioned via the communication pathway of the catheter body. Systems disclosed included integrated closed-loop treatment based on monitored vascular dimension input. Methods included patient optimized treatments incorporating treatment modulation based on dynamic vascular dimension monitoring.

12 Claims, 19 Drawing Sheets

Related U.S. Application Data

(60) Provisional application No. 62/778,657, filed on Dec. 12, 2018.

(51) Int. Cl.

| | |
|---|---|
| *A61B 5/107* | (2006.01) |
| *A61B 8/00* | (2006.01) |
| *A61B 8/06* | (2006.01) |
| *A61B 8/08* | (2006.01) |
| *A61B 8/12* | (2006.01) |
| *A61M 25/04* | (2006.01) |

(52) U.S. Cl.
CPC .......... *A61B 5/6859* (2013.01); *A61B 5/6882* (2013.01); *A61B 8/04* (2013.01); *A61B 8/06* (2013.01); *A61B 8/0891* (2013.01); *A61B 8/12* (2013.01); *A61B 8/4272* (2013.01); *A61B 8/5223* (2013.01); *A61M 25/04* (2013.01); *A61B 8/0858* (2013.01); *A61B 8/4477* (2013.01); *A61B 8/488* (2013.01)

(58) Field of Classification Search
CPC .......... A61B 8/06; A61B 8/0891; A61B 8/12; A61B 8/4272; A61B 8/5223; A61B 8/0858; A61B 8/4477; A61B 8/488; A61M 25/04
See application file for complete search history.

(56) References Cited

U.S. PATENT DOCUMENTS

| | | | |
|---|---|---|---|
| 1,952,161 A | | 3/1934 | Faus |
| 2,133,071 A | | 10/1938 | Anderson |
| 3,209,528 A | | 10/1965 | Zerr |
| 3,568,661 A | | 3/1971 | Franklin |
| 3,838,683 A | | 10/1974 | Kolin |
| 4,142,412 A | | 3/1979 | McLeod |
| 4,638,252 A | | 1/1987 | Bradshaw |
| RE32,361 E | | 2/1987 | Duggan |
| 4,733,669 A | | 3/1988 | Segal |
| 4,893,665 A | | 1/1990 | Reuter |
| 4,926,875 A | | 5/1990 | Rabinovitz et al. |
| 4,947,852 A | | 8/1990 | Nassi et al. |
| 5,127,404 A | | 7/1992 | Wybory et al. |
| 5,205,292 A | | 4/1993 | Czar et al. |
| 5,316,001 A | | 5/1994 | Ferek-Petric et al. |
| 5,327,713 A | | 7/1994 | Sakon |
| 5,339,816 A | | 8/1994 | Akamatsu et al. |
| 5,363,848 A | | 11/1994 | Spani et al. |
| 5,387,235 A | | 2/1995 | Chuter |
| 5,476,484 A | | 12/1995 | Hedberg |
| 5,495,852 A | | 3/1996 | Stadler et al. |
| 5,562,713 A | | 10/1996 | Silvian |
| 5,630,836 A | | 5/1997 | Prem et al. |
| 5,752,522 A | | 5/1998 | Murphy |
| 5,760,341 A | | 6/1998 | Laske |
| 5,852,926 A | | 12/1998 | Breedlove |
| 5,872,520 A | | 2/1999 | Siefert et al. |
| 5,902,308 A | | 5/1999 | Murphy |
| 5,941,198 A | | 8/1999 | Sullivan |
| 5,967,986 A | | 10/1999 | Cimochowski |
| 5,971,933 A | | 10/1999 | Gopakumaran |
| 6,010,511 A | | 1/2000 | Murphy |
| 6,012,457 A | | 1/2000 | Lesh |
| 6,015,386 A | | 1/2000 | Kensey et al. |
| 6,015,387 A | | 1/2000 | Schwartz et al. |
| 6,025,725 A | | 2/2000 | Gershenfeld et al. |
| 6,039,701 A | | 3/2000 | Sliwa et al. |
| 6,053,873 A | | 4/2000 | Govari et al. |
| 6,111,520 A | | 8/2000 | Allen et al. |
| 6,115,633 A | | 9/2000 | Lang et al. |
| 6,115,636 A | | 9/2000 | Ryan |
| 6,164,283 A | | 12/2000 | Lesh |
| 6,165,135 A | | 12/2000 | Neff |
| 6,206,835 B1 | | 3/2001 | Spillman, Jr. et al. |
| 6,231,516 B1 | | 5/2001 | Keilman et al. |
| 6,261,233 B1 | | 7/2001 | Kantorovich |
| 6,272,830 B1 | | 8/2001 | Morgan |
| 6,278,379 B1 | | 8/2001 | Allen et al. |
| 6,287,253 B1 | | 9/2001 | Ortega et al. |
| 6,325,762 B1 | | 12/2001 | Tjin |
| 6,339,816 B1 | | 1/2002 | Bausch |
| 6,354,999 B1 | | 3/2002 | Dgany et al. |
| 6,398,734 B1 | | 6/2002 | Cimochowski et al. |
| 6,434,411 B1 | | 8/2002 | Duret |
| 6,503,202 B1 | | 1/2003 | Hossack et al. |
| 6,574,510 B2 | | 6/2003 | Von Arx et al. |
| 6,673,020 B2 | | 1/2004 | Okada et al. |
| 6,673,596 B1 | | 1/2004 | Sayler |
| 6,699,186 B1 | | 3/2004 | Wolinsky et al. |
| 6,738,671 B2 | | 5/2004 | Christophersom et al. |
| 6,776,763 B2 | | 8/2004 | Nix |
| 6,802,811 B1 | | 10/2004 | Slepian |
| 6,855,115 B2 | | 2/2005 | Fonseca |
| 6,895,265 B2 | | 5/2005 | Silver |
| 6,926,670 B2 | | 8/2005 | Rich et al. |
| 6,972,553 B2 | | 12/2005 | Petrovich et al. |
| 7,065,409 B2 | | 6/2006 | Mazar |
| 7,077,812 B2 | | 7/2006 | Naghavi |
| 7,082,330 B2 | | 7/2006 | Stadler et al. |
| 7,147,604 B1 | | 12/2006 | Allen |
| 7,149,587 B2 | | 12/2006 | Wardle et al. |
| 7,191,013 B1 | | 3/2007 | Miranda et al. |
| 7,225,032 B2 | | 5/2007 | Schmeling et al. |
| 7,233,821 B2 | | 6/2007 | Hettrick |
| 7,236,821 B2 | | 6/2007 | Cates et al. |
| 7,245,117 B1 | | 7/2007 | Joy |
| 7,265,676 B2 | | 9/2007 | Gordon et al. |
| 7,284,442 B2 | | 10/2007 | Fleischman et al. |
| 7,367,984 B2 | | 5/2008 | Kulcinski et al. |
| 7,423,496 B2 | | 9/2008 | Scheuermann |
| 7,432,723 B2 | | 10/2008 | Ellis |
| 7,439,723 B2 | | 10/2008 | Allen |
| 7,444,878 B1 | | 11/2008 | Pepples |
| 7,452,334 B2 | | 11/2008 | Gianchandani et al. |
| 7,454,244 B2 | | 11/2008 | Kassab et al. |
| 7,466,120 B2 | | 12/2008 | Miller |
| 7,479,112 B2 | | 1/2009 | Sweeney et al. |
| 7,481,771 B2 | | 1/2009 | Fonseca |
| 7,492,144 B2 | | 2/2009 | Powers |
| 7,498,799 B2 | | 3/2009 | Allen |
| 7,550,978 B2 | | 6/2009 | Joy |
| 7,574,792 B2 | | 8/2009 | O'Brien |
| 7,595,647 B2 | | 9/2009 | Kroh |
| 7,618,363 B2 | | 11/2009 | Yadav |
| 7,621,036 B2 | | 11/2009 | Cros |
| 7,621,876 B2 | | 11/2009 | Hoctor et al. |
| 7,647,831 B2 | | 1/2010 | Corcoran |
| 7,647,836 B2 | | 1/2010 | O'Brien |
| 7,662,653 B2 | | 2/2010 | O'Brien |
| 7,667,547 B2 | | 2/2010 | Ellis |
| 7,677,107 B2 | | 3/2010 | Nunez |
| 7,678,135 B2 | | 3/2010 | Maahs et al. |
| 7,679,355 B2 | | 3/2010 | Allen |
| 7,699,059 B2 | | 4/2010 | Fonseca |
| 7,710,103 B2 | | 5/2010 | Powers |
| 7,725,160 B2 | | 5/2010 | Weber |
| 7,748,277 B2 | | 7/2010 | O'Brien |
| 7,778,684 B2 | | 8/2010 | Weber et al. |
| 7,786,867 B2 | | 8/2010 | Hamel et al. |
| 7,812,416 B2 | | 10/2010 | Courcimault |
| 7,829,363 B2 | | 11/2010 | You |
| 7,831,301 B2 | | 11/2010 | Webb et al. |
| 7,839,153 B2 | | 11/2010 | Joy |
| 7,848,813 B2 | | 12/2010 | Bergelson et al. |
| 7,854,172 B2 | | 12/2010 | O'Brien |
| 7,899,545 B2 | | 3/2011 | John |
| 7,908,002 B2 | | 3/2011 | Hoijer |
| 7,908,018 B2 | | 3/2011 | O'Brien |
| 7,909,770 B2 | | 3/2011 | Stern |
| 7,932,732 B2 | | 4/2011 | Ellis |
| 7,936,174 B2 | | 5/2011 | Ellis |
| 7,955,269 B2 | | 6/2011 | Stahmann |

(56) References Cited

U.S. PATENT DOCUMENTS

| | | | |
|---|---|---|---|
| 7,966,886 B2 | 6/2011 | Corcoran |
| 7,988,719 B2 | 8/2011 | Alt et al. |
| 8,016,766 B2 | 9/2011 | Goedje et al. |
| 8,021,307 B2 | 9/2011 | White |
| 8,025,625 B2 | 9/2011 | Allen |
| 8,026,729 B2 | 9/2011 | Kroh |
| 8,060,214 B2 | 11/2011 | Larson et al. |
| 8,078,274 B2 | 12/2011 | Kassab |
| 8,082,032 B2 | 12/2011 | Kassab et al. |
| 8,099,161 B2 | 1/2012 | Kassab |
| 8,107,248 B2 | 1/2012 | Shin et al. |
| 8,111,150 B2 | 2/2012 | Miller |
| 8,114,143 B2 | 2/2012 | Kassab et al. |
| 8,118,749 B2 | 2/2012 | White |
| 8,154,389 B2 | 4/2012 | Rowland |
| 8,159,348 B2 | 4/2012 | Ellis |
| 8,185,194 B2 | 5/2012 | Kassab |
| 8,209,033 B2 | 6/2012 | Zhang et al. |
| 8,221,405 B2 | 7/2012 | Whisenant et al. |
| 8,237,451 B2 | 8/2012 | Joy |
| 8,264,240 B2 | 9/2012 | Park |
| 8,267,954 B2 | 9/2012 | Decant, Jr. et al. |
| 8,271,072 B2 | 9/2012 | Houben et al. |
| 8,278,941 B2 | 10/2012 | Kroh |
| 8,298,147 B2 | 10/2012 | Huennekens et al. |
| 8,298,148 B2 | 10/2012 | Furman |
| 8,353,841 B2 | 1/2013 | White |
| 8,355,777 B2 | 1/2013 | White |
| 8,356,399 B2 | 1/2013 | Kaplan |
| 8,360,984 B2 | 1/2013 | Yadar |
| 8,374,689 B2 | 2/2013 | Gopinathan et al. |
| 8,414,495 B2 | 4/2013 | Halmann |
| 8,432,265 B2 | 4/2013 | Rowland |
| 8,442,606 B2 | 5/2013 | Furman |
| 8,442,639 B2 | 5/2013 | Walker et al. |
| 8,465,436 B2 | 6/2013 | Griswold |
| 8,465,452 B2 | 6/2013 | Kassab |
| 8,467,854 B2 | 6/2013 | Lewis et al. |
| 8,480,594 B2 | 7/2013 | Eigler et al. |
| 8,493,187 B2 | 7/2013 | Rowland |
| 8,500,660 B2 | 8/2013 | Buchwald et al. |
| 8,521,282 B2 | 8/2013 | Czygan et al. |
| 8,527,046 B2 | 9/2013 | Connelly et al. |
| 8,556,929 B2 | 10/2013 | Harper et al. |
| 8,570,186 B2 | 10/2013 | Nagy |
| 8,600,517 B2 | 12/2013 | Forsell |
| 8,613,705 B2 | 12/2013 | Scheurer et al. |
| 8,632,469 B2 | 1/2014 | Kassab |
| 8,644,941 B2 | 2/2014 | Rooney et al. |
| 8,665,086 B2 | 3/2014 | Miner |
| 8,669,770 B2 | 3/2014 | Cros |
| 8,696,584 B2 | 4/2014 | Kassab |
| 8,702,613 B2 | 4/2014 | Kassab |
| 8,706,208 B2 | 4/2014 | Chiao et al. |
| 8,706,209 B2 | 4/2014 | Kassab |
| 8,706,219 B2 | 4/2014 | Feldman |
| 8,728,012 B2 | 5/2014 | Braido |
| 8,747,313 B2 | 6/2014 | Tran et al. |
| 8,784,338 B2 | 7/2014 | Wallace |
| 8,798,712 B2 | 8/2014 | Gopinathan et al. |
| 8,814,798 B2 | 8/2014 | Corbucci et al. |
| 8,818,507 B2 | 8/2014 | Liu et al. |
| 8,825,151 B2 | 9/2014 | Gopinathan et al. |
| 8,827,904 B2 | 9/2014 | Ball et al. |
| 8,827,929 B2 | 9/2014 | O'Dea |
| 8,855,783 B2 | 10/2014 | Dagan et al. |
| 8,864,666 B2 | 10/2014 | Kassem |
| 8,870,787 B2 | 10/2014 | Yadav |
| 8,874,203 B2 | 10/2014 | Kassab et al. |
| 8,886,301 B2 | 11/2014 | Kassab |
| 8,894,582 B2 | 11/2014 | Nunez |
| 8,896,324 B2 | 11/2014 | Kroh |
| 8,909,351 B2 | 12/2014 | Dinsmoor et al. |
| 8,918,169 B2 | 12/2014 | Kassab et al. |
| 8,938,292 B2 | 1/2015 | Hettrick et al. |
| 8,951,219 B2 | 2/2015 | Gerber et al. |
| 9,049,995 B2 | 6/2015 | Blomqvist et al. |
| 9,055,917 B2 | 6/2015 | Mann et al. |
| 9,060,798 B2 | 6/2015 | Harper et al. |
| 9,061,099 B2 | 6/2015 | Gerber et al. |
| 9,066,672 B2 | 6/2015 | Kassab et al. |
| 9,089,713 B2 | 7/2015 | John et al. |
| 9,162,065 B2 | 10/2015 | Karst et al. |
| 9,198,706 B2 | 12/2015 | Kassab et al. |
| 9,265,428 B2 | 2/2016 | O'Brien et al. |
| 9,289,132 B2 | 3/2016 | Ghaffari et al. |
| 9,289,229 B2 | 3/2016 | Kassab |
| 9,305,456 B2 | 4/2016 | Rowland |
| 9,314,169 B2 | 4/2016 | Kassab |
| 9,326,728 B2 | 5/2016 | Demir et al. |
| 9,332,914 B2 | 5/2016 | Langston |
| 9,332,916 B2 | 5/2016 | Kassab |
| 9,333,365 B2 | 5/2016 | Zhao |
| 9,351,661 B2 | 5/2016 | Kassab |
| 9,392,940 B2 | 7/2016 | Snichelotto |
| 9,393,416 B2 | 7/2016 | Rooney et al. |
| 9,445,743 B2 | 9/2016 | Kassab |
| 9,489,831 B2 | 11/2016 | Nagy et al. |
| 9,526,637 B2 | 12/2016 | Dagan et al. |
| 9,545,263 B2 | 1/2017 | Lenihan et al. |
| 9,603,533 B2 | 3/2017 | Lading et al. |
| 9,662,066 B2 | 5/2017 | Ledet et al. |
| 9,675,257 B2 | 6/2017 | Kassab |
| 9,675,315 B2 | 6/2017 | Song et al. |
| 9,713,701 B2 | 7/2017 | Sarkar et al. |
| RE46,494 E | 8/2017 | Bauer |
| 9,717,475 B2 | 8/2017 | Corl |
| 9,721,463 B2 | 8/2017 | Rowland |
| 9,724,006 B2 | 8/2017 | Dumont et al. |
| 9,788,739 B2 | 10/2017 | John et al. |
| 9,814,395 B2 | 11/2017 | Stahmann et al. |
| 9,820,673 B2 | 11/2017 | Feldman |
| 9,872,948 B2 | 1/2018 | Siess |
| 9,878,080 B2 | 1/2018 | Kaiser et al. |
| 9,901,722 B2 | 2/2018 | Nitzan et al. |
| 9,996,712 B2 | 6/2018 | Sundaram et al. |
| 10,080,528 B2 | 9/2018 | BeBusschere et al. |
| 10,092,247 B2 | 10/2018 | Taylor |
| 10,105,103 B2 | 10/2018 | Goldshtein et al. |
| 10,194,808 B1 | 2/2019 | Thompson |
| 10,195,441 B2 | 2/2019 | Kaiser |
| 10,201,285 B2 | 2/2019 | Sawanoi |
| 10,210,956 B2 | 2/2019 | Lavi |
| 10,213,129 B2 | 2/2019 | Kassab |
| 10,219,704 B2 | 3/2019 | Lavi et al. |
| 10,219,720 B2 | 3/2019 | Kassab |
| 10,219,724 B2 | 3/2019 | Stern |
| 10,226,203 B2 | 3/2019 | Stigall |
| 10,226,218 B2 | 3/2019 | Rowland |
| 10,231,659 B2 | 3/2019 | Vanslyke |
| 10,231,701 B2 | 3/2019 | Ryan |
| 10,236,084 B2 | 3/2019 | Grady |
| 10,238,311 B2 | 3/2019 | Kassab |
| 10,238,322 B2 | 3/2019 | Vanslyke |
| 10,238,323 B2 | 3/2019 | Vanslyke |
| 10,238,324 B2 | 3/2019 | Vanslyke |
| 10,240,994 B1 | 3/2019 | Xu |
| 10,265,024 B2 | 4/2019 | Lee |
| 10,271,797 B2 | 4/2019 | Zhang |
| 10,335,042 B2 | 7/2019 | Schoenie et al. |
| 10,390,714 B2 | 8/2019 | Wolinsky |
| 10,433,736 B2 | 10/2019 | Karlovsky et al. |
| 10,537,281 B2 | 1/2020 | Thompson et al. |
| 10,542,887 B2 | 1/2020 | Sarkar et al. |
| 10,548,535 B2 | 2/2020 | Zhang et al. |
| 10,555,704 B2 | 2/2020 | Averina et al. |
| 10,582,866 B2 | 3/2020 | Badie et al. |
| 10,588,528 B2 | 3/2020 | Banet et al. |
| 10,595,734 B2 | 3/2020 | Thakur et al. |
| 10,596,381 B2 | 3/2020 | Averina et al. |
| 10,638,980 B2 | 5/2020 | Gyllensten et al. |
| 10,660,577 B2 | 5/2020 | Thakur et al. |
| 10,687,715 B2 | 6/2020 | Jansen et al. |
| 10,702,213 B2 | 7/2020 | Sharma et al. |

(56) References Cited

U.S. PATENT DOCUMENTS

| | | | |
|---|---|---|---|
| 10,806,352 B2 | 10/2020 | Sweeney et al. |
| 10,905,393 B2 | 2/2021 | Gifford, III et al. |
| 11,006,845 B2 | 5/2021 | Kuraguntla et al. |
| 11,039,813 B2 | 6/2021 | Gifford, III et al. |
| 11,206,992 B2 | 12/2021 | Sweeney et al. |
| 11,272,840 B2 | 3/2022 | Rothfuss |
| 11,445,924 B2 | 9/2022 | Joseph |
| 11,452,497 B2 | 9/2022 | Garza |
| 11,564,596 B2 | 1/2023 | Gifford et al. |
| 11,890,082 B2 | 2/2024 | Cros et al. |
| 2001/0047198 A1 | 11/2001 | Drasler et al. |
| 2002/0120205 A1 | 8/2002 | Ferek-Petric |
| 2002/0188207 A1 | 12/2002 | Richter |
| 2003/0037591 A1 | 2/2003 | Ashton et al. |
| 2003/0100940 A1 | 5/2003 | Yodfat |
| 2003/0125797 A1 | 7/2003 | Chobotov |
| 2003/0135971 A1 | 7/2003 | Liberman |
| 2003/0158584 A1 | 8/2003 | Cates et al. |
| 2003/0199938 A1 | 10/2003 | Smits et al. |
| 2003/0216803 A1 | 11/2003 | Ledergerber |
| 2004/0054287 A1 | 3/2004 | Stephens |
| 2004/0106871 A1 | 6/2004 | Hunyor et al. |
| 2004/0116992 A1 | 6/2004 | Wardle |
| 2004/0133092 A1 | 7/2004 | Kain |
| 2004/0140939 A1 | 7/2004 | Haller et al. |
| 2004/0167596 A1 | 8/2004 | Richter |
| 2004/0176672 A1 | 9/2004 | Silver et al. |
| 2004/0215235 A1 | 10/2004 | Jackson et al. |
| 2004/0225326 A1 | 11/2004 | Weiner |
| 2005/0049686 A1 | 3/2005 | Gray et al. |
| 2005/0049689 A1 | 3/2005 | Gray |
| 2005/0137481 A1 | 6/2005 | Sheard et al. |
| 2005/0148903 A1 | 7/2005 | Diamantopoulos |
| 2005/0149119 A1 | 7/2005 | Koyfman |
| 2005/0154321 A1 | 7/2005 | Wolinsky |
| 2005/0177224 A1 | 8/2005 | Fogarty |
| 2005/0228486 A1 | 10/2005 | Case |
| 2006/0047327 A1 | 3/2006 | Colvin et al. |
| 2006/0056161 A1 | 3/2006 | Shin |
| 2006/0079793 A1 | 4/2006 | Mann |
| 2006/0100522 A1 | 5/2006 | Yuan et al. |
| 2006/0106321 A1 | 5/2006 | Lewinsky et al. |
| 2006/0122522 A1 | 6/2006 | Chavan et al. |
| 2006/0149166 A1 | 7/2006 | Zvuloni |
| 2006/0174712 A1 | 8/2006 | O'Brien |
| 2006/0177956 A1 | 8/2006 | O'Brien |
| 2006/0178695 A1 | 8/2006 | Decant |
| 2006/0207414 A1 | 9/2006 | Nye |
| 2006/0253160 A1 | 11/2006 | Benditt et al. |
| 2006/0271119 A1 | 11/2006 | Ni et al. |
| 2006/0280351 A1 | 12/2006 | Luping et al. |
| 2006/0287602 A1 | 12/2006 | Obrien et al. |
| 2006/0287700 A1 | 12/2006 | White |
| 2007/0043409 A1 | 2/2007 | Brian |
| 2007/0088214 A1 | 4/2007 | Shuros |
| 2007/0129637 A1 | 6/2007 | Wolinsky et al. |
| 2007/0158769 A1 | 7/2007 | You |
| 2007/0199385 A1 | 8/2007 | O'Brien |
| 2007/0238998 A1 | 10/2007 | Nycz et al. |
| 2007/0247138 A1 | 10/2007 | Miller et al. |
| 2007/0249950 A1 | 10/2007 | Piaget et al. |
| 2007/0274565 A1 | 11/2007 | Penner |
| 2007/0282210 A1 | 12/2007 | Stern |
| 2007/0292090 A1 | 12/2007 | Alphonse et al. |
| 2008/0015569 A1 | 1/2008 | Saadat |
| 2008/0033527 A1 | 2/2008 | Nunez et al. |
| 2008/0077016 A1 | 3/2008 | Sparks |
| 2008/0097227 A1 | 4/2008 | Zdeblick et al. |
| 2008/0177186 A1 | 7/2008 | Slater et al. |
| 2008/0275350 A1 | 11/2008 | Liao |
| 2008/0287800 A1 | 11/2008 | Furman |
| 2008/0294041 A1 | 11/2008 | Kassab |
| 2008/0306580 A1 | 12/2008 | Jenson |
| 2009/0005803 A1 | 1/2009 | Batiste |
| 2009/0007679 A1 | 1/2009 | Nunez |
| 2009/0009332 A1 | 1/2009 | Nunez |
| 2009/0011117 A1 | 1/2009 | Nunez |
| 2009/0024029 A1 | 1/2009 | Murashita |
| 2009/0024042 A1 | 1/2009 | Nunez |
| 2009/0024177 A1 | 1/2009 | Shuros et al. |
| 2009/0030291 A1 | 1/2009 | O'Brien |
| 2009/0036776 A1 | 2/2009 | Masuda et al. |
| 2009/0062684 A1 | 3/2009 | Gregersen et al. |
| 2009/0105799 A1 | 4/2009 | Hekmat et al. |
| 2009/0149766 A1 | 6/2009 | Shuros et al. |
| 2009/0177225 A1 | 7/2009 | Nunez et al. |
| 2009/0189741 A1 | 7/2009 | Rowland |
| 2009/0198293 A1 | 8/2009 | Cauller |
| 2009/0270729 A1 | 10/2009 | Corbucci |
| 2009/0299427 A1 | 12/2009 | Liu et al. |
| 2009/0306507 A1 | 12/2009 | Hyun et al. |
| 2010/0056922 A1 | 3/2010 | Florent |
| 2010/0063375 A1 | 3/2010 | Kassab et al. |
| 2010/0076398 A1 | 3/2010 | Scheurer et al. |
| 2010/0076543 A1 | 3/2010 | Melsheimer |
| 2010/0094328 A1 | 4/2010 | O'dea et al. |
| 2010/0113939 A1 | 5/2010 | Mashimo et al. |
| 2010/0121398 A1 | 5/2010 | Bjorling et al. |
| 2010/0168577 A1 | 7/2010 | Vezina |
| 2010/0222786 A1 | 9/2010 | Kassab |
| 2010/0262021 A1 | 10/2010 | Yadav |
| 2010/0262206 A1 | 10/2010 | Zdeblick et al. |
| 2010/0274217 A1 | 10/2010 | Da Silva et al. |
| 2010/0324432 A1 | 12/2010 | Bjorling et al. |
| 2010/0324665 A1 | 12/2010 | Shaw |
| 2010/0331754 A1* | 12/2010 | Fulkerson .............. A61B 5/412 |
| | | 604/6.09 |
| 2011/0054333 A1 | 3/2011 | Hoffer |
| 2011/0105863 A1 | 5/2011 | Kroh |
| 2011/0144967 A1 | 6/2011 | Adirovich |
| 2011/0160844 A1 | 6/2011 | Haselby |
| 2011/0178383 A1 | 7/2011 | Kassab |
| 2011/0184301 A1 | 7/2011 | Holmstrom et al. |
| 2011/0201990 A1 | 8/2011 | Franano |
| 2011/0214898 A1 | 9/2011 | Huynh |
| 2011/0224529 A1 | 9/2011 | Lading |
| 2011/0224582 A1 | 9/2011 | Spence |
| 2011/0265908 A1 | 11/2011 | Clerc et al. |
| 2011/0306867 A1 | 12/2011 | Gopinathan et al. |
| 2012/0016207 A1 | 1/2012 | Allen |
| 2012/0029598 A1 | 2/2012 | Zhao |
| 2012/0136385 A1 | 5/2012 | Cully |
| 2012/0197118 A1 | 8/2012 | Lisiecki et al. |
| 2012/0203090 A1 | 8/2012 | Min |
| 2012/0203113 A1 | 8/2012 | Skerl et al. |
| 2012/0283811 A1 | 11/2012 | Neilan |
| 2012/0291788 A1 | 11/2012 | Griswold et al. |
| 2012/0296222 A1 | 11/2012 | Griswold et al. |
| 2013/0023981 A1 | 1/2013 | Dierking |
| 2013/0030295 A1 | 1/2013 | Huennekens et al. |
| 2013/0041244 A1 | 2/2013 | Woias et al. |
| 2013/0041251 A1 | 2/2013 | Bailey et al. |
| 2013/0041269 A1 | 2/2013 | Stahmann et al. |
| 2013/0060139 A1 | 3/2013 | Richter |
| 2013/0073025 A1 | 3/2013 | Kassab |
| 2013/0085350 A1 | 4/2013 | Schugt et al. |
| 2013/0096409 A1 | 4/2013 | Hiltner et al. |
| 2013/0167502 A1 | 7/2013 | Wilson |
| 2013/0178750 A1 | 7/2013 | Sheehan et al. |
| 2013/0178751 A1 | 7/2013 | Min |
| 2013/0184545 A1 | 7/2013 | Blomqvist et al. |
| 2013/0192611 A1 | 8/2013 | Taepke, II |
| 2013/0211291 A1 | 8/2013 | Tran |
| 2013/0218054 A1 | 8/2013 | Sverdlik et al. |
| 2013/0222153 A1 | 8/2013 | Rowland et al. |
| 2013/0245469 A1 | 9/2013 | Yadav |
| 2013/0245745 A1 | 9/2013 | Vong et al. |
| 2013/0261655 A1 | 10/2013 | Drasler et al. |
| 2013/0274705 A1 | 10/2013 | Burnes et al. |
| 2013/0281800 A1 | 10/2013 | Saroka et al. |
| 2013/0289703 A1 | 10/2013 | Kinkade et al. |
| 2013/0296721 A1 | 11/2013 | Yadav et al. |
| 2013/0303914 A1 | 11/2013 | Hiltner et al. |
| 2013/0303915 A1 | 11/2013 | Barnard et al. |

(56) References Cited

U.S. PATENT DOCUMENTS

| | | |
|---|---|---|
| 2013/0306232 A1 | 11/2013 | Hedberg |
| 2013/0310820 A1 | 11/2013 | Fernandez et al. |
| 2013/0317359 A1 | 11/2013 | Wilson et al. |
| 2013/0324866 A1 | 12/2013 | Gladshtein |
| 2013/0331678 A1 | 12/2013 | Lading et al. |
| 2013/0338468 A1 | 12/2013 | Kassab |
| 2013/0345650 A1 | 12/2013 | Amirouche |
| 2014/0028467 A1 | 1/2014 | Nagy |
| 2014/0051965 A1 | 2/2014 | Zdeblick et al. |
| 2014/0066738 A1 | 3/2014 | Kassab |
| 2014/0073935 A1 | 3/2014 | Rodriguez-Llorente |
| 2014/0084943 A1 | 3/2014 | Kroh |
| 2014/0088994 A1 | 3/2014 | Kroh |
| 2014/0094697 A1 | 4/2014 | Petroff et al. |
| 2014/0107768 A1 | 4/2014 | Venkatasubramanian |
| 2014/0155710 A1 | 6/2014 | Rowland |
| 2014/0155768 A1 | 6/2014 | Orion et al. |
| 2014/0155769 A1 | 6/2014 | White |
| 2014/0180118 A1 | 6/2014 | Stigall |
| 2014/0187977 A1 | 7/2014 | Lading |
| 2014/0188011 A1 | 7/2014 | Wurster et al. |
| 2014/0188127 A1 | 7/2014 | Dubrul |
| 2014/0200428 A1 | 7/2014 | Kassab |
| 2014/0236011 A1 | 8/2014 | Fan et al. |
| 2014/0243640 A1 | 8/2014 | O'Dea |
| 2014/0266935 A1 | 9/2014 | Tankiewicz |
| 2014/0275861 A1 | 9/2014 | Kroh |
| 2014/0276011 A1 | 9/2014 | Schmitt et al. |
| 2014/0276067 A1 | 9/2014 | Neasham |
| 2014/0276110 A1 | 9/2014 | Hoseit |
| 2014/0276121 A1 | 9/2014 | Kassab |
| 2014/0276191 A1 | 9/2014 | Kassab |
| 2014/0276234 A1 | 9/2014 | Hines |
| 2014/0288085 A1 | 9/2014 | Yadav |
| 2014/0288459 A1 | 9/2014 | Yadav |
| 2014/0306807 A1 | 10/2014 | Rowland |
| 2014/0330143 A1 | 11/2014 | Kroh et al. |
| 2014/0350348 A1 | 11/2014 | Tee et al. |
| 2014/0371624 A1 | 12/2014 | Ziaie |
| 2015/0031966 A1 | 1/2015 | Ward et al. |
| 2015/0045649 A1 | 2/2015 | O'Dea et al. |
| 2015/0051467 A1 | 2/2015 | Corbucci et al. |
| 2015/0065835 A1 | 3/2015 | Kassab |
| 2015/0065897 A1 | 3/2015 | Bomzin et al. |
| 2015/0088100 A1 | 3/2015 | Oborn |
| 2015/0133796 A1 | 5/2015 | Yadav |
| 2015/0141863 A1 | 5/2015 | Kassab et al. |
| 2015/0157268 A1 | 6/2015 | Winshtein et al. |
| 2015/0208929 A1 | 7/2015 | Rowland |
| 2015/0216425 A1 | 8/2015 | Gladshtein et al. |
| 2015/0223702 A1 | 8/2015 | Vanney et al. |
| 2015/0238121 A1 | 8/2015 | Tu et al. |
| 2015/0257732 A1 | 9/2015 | Ryan |
| 2015/0282720 A1 | 10/2015 | Goldshtein et al. |
| 2015/0282875 A1 | 10/2015 | Harper et al. |
| 2015/0290373 A1 | 10/2015 | Rudser et al. |
| 2015/0297110 A1 | 10/2015 | Kassab |
| 2015/0297111 A1 | 10/2015 | Kassab |
| 2015/0297112 A1 | 10/2015 | Kassab et al. |
| 2015/0297113 A1 | 10/2015 | Kassab |
| 2015/0297818 A1 | 10/2015 | Matsubara et al. |
| 2015/0305808 A1 | 10/2015 | Ku et al. |
| 2015/0313479 A1 | 11/2015 | Stigall et al. |
| 2015/0327786 A1 | 11/2015 | Lading et al. |
| 2016/0000403 A1 | 1/2016 | Vilkomerson |
| 2016/0015507 A1 | 1/2016 | Johnson et al. |
| 2016/0022216 A1 | 1/2016 | Goldshtein et al. |
| 2016/0022447 A1 | 1/2016 | Kim et al. |
| 2016/0029956 A1 | 2/2016 | Rowland |
| 2016/0029995 A1 | 2/2016 | Navratil et al. |
| 2016/0038087 A1 | 2/2016 | Hunter |
| 2016/0045184 A1 | 2/2016 | Courtney |
| 2016/0064117 A1 | 3/2016 | Romero |
| 2016/0081657 A1 | 3/2016 | Rice |
| 2016/0095535 A1 | 4/2016 | Hettrick et al. |
| 2016/0135787 A1 | 5/2016 | Anderson et al. |
| 2016/0135941 A1 | 5/2016 | Binmoeller et al. |
| 2016/0166232 A1 | 6/2016 | Merritt |
| 2016/0198981 A1 | 7/2016 | Demir et al. |
| 2016/0199204 A1 | 7/2016 | Pung |
| 2016/0210846 A1 | 7/2016 | Rowland et al. |
| 2016/0324443 A1 | 11/2016 | Rowland et al. |
| 2016/0345930 A1 | 12/2016 | Mizukami |
| 2016/0354032 A1 | 12/2016 | Wariar |
| 2016/0374710 A1 | 12/2016 | Sinelnikov |
| 2017/0027458 A1* | 2/2017 | Glover ................. A61B 5/6851 |
| 2017/0055048 A1 | 2/2017 | Nagy et al. |
| 2017/0055909 A1 | 3/2017 | Schibli et al. |
| 2017/0065186 A1 | 3/2017 | Joseph et al. |
| 2017/0065824 A1 | 3/2017 | Dagan et al. |
| 2017/0071501 A1 | 3/2017 | Kassab |
| 2017/0091574 A1 | 3/2017 | Udupa |
| 2017/0127975 A1 | 5/2017 | Bozkurt |
| 2017/0164840 A1 | 6/2017 | Matsumoto |
| 2017/0181677 A1 | 6/2017 | Varsavsky et al. |
| 2017/0211229 A1 | 7/2017 | Nozaki |
| 2017/0216508 A1 | 8/2017 | Zilbershlag et al. |
| 2017/0224279 A1 | 8/2017 | Cahan et al. |
| 2017/0232798 A1 | 8/2017 | Suzuki |
| 2017/0238817 A1 | 8/2017 | Lading |
| 2017/0290686 A1 | 10/2017 | Sirhan et al. |
| 2017/0319096 A1 | 11/2017 | Kaiser |
| 2017/0332945 A1 | 11/2017 | Gopinathan et al. |
| 2017/0340440 A1 | 11/2017 | Ratz |
| 2017/0360312 A1 | 12/2017 | Joseph |
| 2018/0014829 A1 | 1/2018 | Tal et al. |
| 2018/0055386 A1 | 3/2018 | Zielinski |
| 2018/0064931 A1 | 3/2018 | Clements |
| 2018/0092631 A1 | 4/2018 | Liou |
| 2018/0132724 A1 | 5/2018 | Waechter-Stehle |
| 2018/0140851 A1 | 5/2018 | Maile |
| 2018/0172785 A1 | 6/2018 | Leussler et al. |
| 2018/0177486 A1 | 6/2018 | Gifford et al. |
| 2018/0220992 A1 | 8/2018 | Gifford et al. |
| 2018/0228951 A1 | 8/2018 | Schwammenthal et al. |
| 2018/0247095 A1 | 8/2018 | Sundaram et al. |
| 2018/0268941 A1 | 9/2018 | Lavi et al. |
| 2018/0269931 A1 | 9/2018 | Hershko et al. |
| 2018/0271371 A1 | 9/2018 | Ziaie et al. |
| 2018/0289488 A1 | 10/2018 | Orth et al. |
| 2018/0289536 A1 | 10/2018 | Burnett |
| 2018/0293409 A1 | 10/2018 | Sundaram et al. |
| 2018/0303414 A1 | 10/2018 | Toth |
| 2018/0326151 A1 | 11/2018 | Halpert et al. |
| 2018/0344917 A1 | 12/2018 | Inhaber et al. |
| 2019/0015013 A1 | 1/2019 | Zhu et al. |
| 2019/0029639 A1 | 1/2019 | Gifford et al. |
| 2019/0046047 A1 | 2/2019 | Haase |
| 2019/0053720 A1 | 2/2019 | Sawado |
| 2019/0053767 A1 | 2/2019 | Yamada |
| 2019/0059777 A1 | 2/2019 | Aga et al. |
| 2019/0069784 A1 | 3/2019 | Mukkamala |
| 2019/0069842 A1 | 3/2019 | Rothberg |
| 2019/0069851 A1 | 3/2019 | Sharma |
| 2019/0070348 A1 | 3/2019 | Frost |
| 2019/0076033 A1 | 3/2019 | Sweeney et al. |
| 2019/0082978 A1 | 3/2019 | Van der Horst |
| 2019/0083030 A1 | 3/2019 | Thakur |
| 2019/0090760 A1 | 3/2019 | Kinast |
| 2019/0090763 A1 | 3/2019 | Woerlee |
| 2019/0090856 A1 | 3/2019 | Van der Horst |
| 2019/0099087 A1 | 4/2019 | Cros |
| 2019/0099088 A1 | 4/2019 | Whinnett |
| 2019/0110696 A1 | 4/2019 | Benkowski |
| 2019/0126014 A1 | 5/2019 | Kapur et al. |
| 2019/0150882 A1 | 5/2019 | Maharbiz et al. |
| 2019/0150884 A1 | 5/2019 | Maharbiz et al. |
| 2019/0167188 A1 | 6/2019 | Gifford et al. |
| 2019/0175035 A1 | 6/2019 | van der Horst et al. |
| 2019/0183354 A1 | 6/2019 | Rowe |
| 2019/0358393 A1 | 11/2019 | Marbet |
| 2019/0390403 A1 | 12/2019 | Waterbury |
| 2020/0000364 A1 | 1/2020 | Doodeman et al. |
| 2020/0013510 A1 | 1/2020 | Despenic et al. |

(56) References Cited

U.S. PATENT DOCUMENTS

| | | | |
|---|---|---|---|
| 2020/0022588 A1 | 1/2020 | Wariar et al. |
| 2020/0022589 A1 | 1/2020 | Banet et al. |
| 2020/0029829 A1 | 1/2020 | Banet et al. |
| 2020/0029857 A1 | 1/2020 | Rowland et al. |
| 2020/0030612 A1 | 1/2020 | Song et al. |
| 2020/0037888 A1 | 2/2020 | Thakur et al. |
| 2020/0037892 A1 | 2/2020 | Banet et al. |
| 2020/0046299 A1 | 2/2020 | An et al. |
| 2020/0069857 A1 | 3/2020 | Schwammenthal et al. |
| 2020/0121187 A1 | 4/2020 | Sarkar et al. |
| 2020/0123703 A1 | 4/2020 | Smith |
| 2020/0129087 A1 | 4/2020 | Sweeney et al. |
| 2020/0131699 A1 | 4/2020 | Obana |
| 2020/0146577 A1 | 5/2020 | Badie et al. |
| 2020/0170515 A1 | 6/2020 | Wen et al. |
| 2020/0170711 A1 | 6/2020 | Hendriks et al. |
| 2020/0187864 A1 | 6/2020 | Sharma |
| 2020/0187865 A1 | 6/2020 | Sharma et al. |
| 2020/0196876 A1 | 6/2020 | Minor et al. |
| 2020/0196899 A1 | 6/2020 | Higgins et al. |
| 2020/0196943 A1 | 6/2020 | Minor et al. |
| 2020/0196944 A1 | 6/2020 | Minor et al. |
| 2020/0196948 A1 | 6/2020 | Cho et al. |
| 2020/0197178 A1 | 6/2020 | Vecchio |
| 2020/0254161 A1 | 8/2020 | Schwammenthal et al. |
| 2020/0289257 A1 | 9/2020 | Marquez |
| 2020/0345246 A1 | 11/2020 | Hilgers et al. |
| 2021/0038094 A1 | 2/2021 | Sweeney et al. |
| 2021/0060298 A1 | 3/2021 | Arndt et al. |
| 2021/0113099 A1 | 4/2021 | Rogers et al. |
| 2021/0113194 A1 | 4/2021 | Padwal et al. |
| 2021/0177277 A1 | 6/2021 | Cros et al. |
| 2021/0216733 A1 | 7/2021 | Chronos et al. |
| 2021/0244381 A1 | 8/2021 | Sweeney et al. |
| 2021/0254279 A1 | 8/2021 | Obana |
| 2021/0401306 A1 | 12/2021 | Sweeney |
| 2022/0071488 A1 | 3/2022 | Andersen et al. |
| 2022/0125312 A1 | 4/2022 | Nazari et al. |
| 2022/0193419 A1 | 6/2022 | Sarkar et al. |
| 2022/0233084 A1 | 7/2022 | Valdez |
| 2022/0240792 A1 | 8/2022 | Wetterling |
| 2022/0265157 A1 | 8/2022 | Charthad |
| 2023/0277157 A1 | 9/2023 | Garcia et al. |
| 2024/0155147 A1 | 5/2024 | Sun et al. |

FOREIGN PATENT DOCUMENTS

| | | | |
|---|---|---|---|
| CN | 110613449 B | 5/2020 |
| CN | 111867672 A | 10/2020 |
| DE | 102005035022 A1 | 11/2006 |
| EP | 0399059 A1 | 5/1989 |
| EP | 0538885 A1 | 4/1993 |
| EP | 0897285 A1 | 2/1999 |
| EP | 1162914 A1 | 12/2001 |
| EP | 1311210 A2 | 5/2003 |
| EP | 0904009 B1 | 9/2003 |
| EP | 1545303 A2 | 6/2005 |
| EP | 1677852 A2 | 7/2006 |
| EP | 1847217 A2 | 10/2007 |
| EP | 1851524 A2 | 11/2007 |
| EP | 1851791 A2 | 11/2007 |
| EP | 1868496 A2 | 12/2007 |
| EP | 1871224 A2 | 1/2008 |
| EP | 1893080 A2 | 3/2008 |
| EP | 1893081 A2 | 3/2008 |
| EP | 1893085 A2 | 3/2008 |
| EP | 2091426 A2 | 6/2008 |
| EP | 1948007 | 7/2008 |
| EP | 1993438 A1 | 11/2008 |
| EP | 2012658 A2 | 1/2009 |
| EP | 2046242 A2 | 4/2009 |
| EP | 2117423 A2 | 11/2009 |
| EP | 2197344 A1 | 6/2010 |
| EP | 2265164 A1 | 12/2010 |
| EP | 2021757 B1 | 4/2011 |
| EP | 2391263 A2 | 12/2011 |
| EP | 1921983 B1 | 1/2012 |
| EP | 2060014 B1 | 1/2012 |
| EP | 1902529 B1 | 6/2012 |
| EP | 1876945 B1 | 12/2012 |
| EP | 2330968 B1 | 4/2013 |
| EP | 2601633 A2 | 6/2013 |
| EP | 2449960 B1 | 10/2013 |
| EP | 2725969 A1 | 5/2014 |
| EP | 1993436 B1 | 6/2014 |
| EP | 3027109 A1 | 2/2015 |
| EP | 2076170 B1 | 4/2015 |
| EP | 2895059 A1 | 7/2015 |
| EP | 2898470 A1 | 7/2015 |
| EP | 2922465 A1 | 9/2015 |
| EP | 2317912 B1 | 11/2015 |
| EP | 1817593 B1 | 12/2015 |
| EP | 2967432 A2 | 1/2016 |
| EP | 2268218 B1 | 2/2016 |
| EP | 2456502 B1 | 4/2016 |
| EP | 2702578 B1 | 8/2016 |
| EP | 3057075 A1 | 8/2016 |
| EP | 2417590 B1 | 5/2017 |
| EP | 2986252 B1 | 7/2018 |
| EP | 3359021 A1 | 8/2018 |
| EP | 3435847 A1 | 2/2019 |
| EP | 3435862 A1 | 2/2019 |
| EP | 3437000 A1 | 2/2019 |
| EP | 3448330 A1 | 3/2019 |
| EP | 3448487 A2 | 3/2019 |
| EP | 3457911 A1 | 3/2019 |
| EP | 3457924 A1 | 3/2019 |
| EP | 3457928 A1 | 3/2019 |
| EP | 3463082 A1 | 4/2019 |
| EP | 3468462 A1 | 4/2019 |
| EP | 3591663 A1 | 1/2020 |
| EP | 3609392 A1 | 2/2020 |
| EP | 3256043 B1 | 3/2020 |
| EP | 3629921 A1 | 4/2020 |
| EP | 3629937 A1 | 4/2020 |
| EP | 3630275 A1 | 4/2020 |
| EP | 3634206 A1 | 4/2020 |
| EP | 3654835 A1 | 5/2020 |
| EP | 3496808 B1 | 6/2020 |
| EP | 2654560 B1 | 7/2020 |
| EP | 3326524 B1 | 7/2020 |
| EP | 3367884 B1 | 7/2020 |
| EP | 3678539 A1 | 7/2020 |
| EP | 3681389 A1 | 7/2020 |
| EP | 3684260 A1 | 7/2020 |
| EP | 3684464 A1 | 7/2020 |
| EP | 2155307 B1 | 3/2021 |
| EP | 4039173 A1 | 8/2022 |
| FR | 3119090 A1 | 7/2022 |
| GB | 2473529 A | 3/2011 |
| JP | 2011234884 A | 11/2011 |
| JP | 2024516492 A | 4/2024 |
| WO | 1997042871 A1 | 11/1997 |
| WO | 1998029030 A1 | 12/1997 |
| WO | 1998035611 A1 | 8/1998 |
| WO | 2000055579 A2 | 9/2000 |
| WO | 2000056210 A1 | 9/2000 |
| WO | 2001012092 A1 | 2/2001 |
| WO | 2001013792 A1 | 3/2001 |
| WO | 2002015823 A2 | 2/2002 |
| WO | 2002076289 A2 | 10/2002 |
| WO | 2003061467 A1 | 7/2003 |
| WO | 2003061504 A1 | 7/2003 |
| WO | 2003092495 A1 | 11/2003 |
| WO | 2004073796 A1 | 9/2004 |
| WO | 2006049796 A2 | 5/2006 |
| WO | 2006086113 A2 | 8/2006 |
| WO | 2006086114 A2 | 8/2006 |
| WO | 2005027998 A2 | 9/2006 |
| WO | 2006094273 A2 | 9/2006 |
| WO | 2006096582 A1 | 9/2006 |
| WO | 2006102905 A1 | 10/2006 |
| WO | 2006110798 A2 | 10/2006 |
| WO | 200625215 A2 | 11/2006 |

(56)　　　　　References Cited

FOREIGN PATENT DOCUMENTS

| WO | 2006125215 | A2 | 11/2006 |
| WO | 2007002185 | A2 | 1/2007 |
| WO | 2007002224 | A2 | 1/2007 |
| WO | 2007002225 | A2 | 1/2007 |
| WO | 2007008493 | A1 | 1/2007 |
| WO | 2007028035 | A2 | 3/2007 |
| WO | 2007035332 | A1 | 3/2007 |
| WO | 2007047571 | A2 | 4/2007 |
| WO | 2007047794 | A2 | 4/2007 |
| WO | 2007061841 | A2 | 5/2007 |
| WO | 2007106490 | A2 | 9/2007 |
| WO | 2007106533 | A1 | 9/2007 |
| WO | 2007130628 | A2 | 11/2007 |
| WO | 2008031011 | A1 | 3/2008 |
| WO | 2008031095 | A1 | 3/2008 |
| WO | 2008051907 | A1 | 5/2008 |
| WO | 2008066569 | A2 | 6/2008 |
| WO | 2009006602 | A1 | 1/2009 |
| WO | 2009006608 | A1 | 1/2009 |
| WO | 2009006610 | A1 | 1/2009 |
| WO | 2009006615 | A1 | 1/2009 |
| WO | 2009025648 | A1 | 2/2009 |
| WO | 2009039174 | A1 | 3/2009 |
| WO | 2009111255 | A1 | 9/2009 |
| WO | 2009131879 | A1 | 10/2009 |
| WO | 2011060359 | A2 | 11/2009 |
| WO | 2009146089 | A2 | 12/2009 |
| WO | 2009146090 | A1 | 12/2009 |
| WO | 2009149462 | A2 | 12/2009 |
| WO | 2010011612 | A1 | 1/2010 |
| WO | 2010088279 | A2 | 8/2010 |
| WO | 2010117597 | A1 | 10/2010 |
| WO | 20100117356 | A1 | 10/2010 |
| WO | 2011011104 | A1 | 1/2011 |
| WO | 2012015954 | A1 | 2/2012 |
| WO | 2012015955 | A1 | 2/2012 |
| WO | 2012019191 | A2 | 2/2012 |
| WO | 2012090206 | A2 | 7/2012 |
| WO | 2012140147 | A3 | 10/2012 |
| WO | 2012145187 | A1 | 10/2012 |
| WO | 2012149008 | A2 | 11/2012 |
| WO | 2013003754 | A1 | 1/2013 |
| WO | 2013142387 | A1 | 9/2013 |
| WO | 2013163605 | A1 | 10/2013 |
| WO | 2014006471 | A2 | 1/2014 |
| WO | 2014012670 | A1 | 1/2014 |
| WO | 2004014456 | A2 | 2/2014 |
| WO | 2014047528 | A1 | 3/2014 |
| WO | 2014054045 | A1 | 4/2014 |
| WO | 2014070316 | A1 | 5/2014 |
| WO | 2014076620 | A2 | 5/2014 |
| WO | 2014081958 | A1 | 5/2014 |
| WO | 2014145531 | A1 | 9/2014 |
| WO | 2014145712 | A1 | 9/2014 |
| WO | 2014162181 | A2 | 10/2014 |
| WO | 2014170771 | A1 | 10/2014 |
| WO | 2014179739 | A1 | 11/2014 |
| WO | 2014188430 | A2 | 11/2014 |
| WO | 2014197101 | A1 | 12/2014 |
| WO | 2015074018 | A1 | 5/2015 |
| WO | 2015109028 | A1 | 7/2015 |
| WO | 20150157712 | A2 | 10/2015 |
| WO | 2016011309 | A2 | 1/2016 |
| WO | 2016025430 | A1 | 2/2016 |
| WO | 2016039761 | A1 | 3/2016 |
| WO | WO-2016131020 | A1 * | 8/2016 | ........... A61B 5/1076 |
| WO | 2016156446 | A1 | 10/2016 |
| WO | 2016178196 | A2 | 11/2016 |
| WO | 2016178197 | A1 | 11/2016 |
| WO | 2017024051 | A1 | 2/2017 |
| WO | 2017143198 | A1 | 8/2017 |
| WO | 2017198867 | A1 | 11/2017 |
| WO | 2017200956 | A1 | 11/2017 |
| WO | 2017222964 | A1 | 12/2017 |
| WO | 2018013725 | A1 | 1/2018 |
| WO | 2018031714 | A1 | 2/2018 |
| WO | 2018081314 | A1 | 5/2018 |
| WO | 2018102435 | A1 | 6/2018 |
| WO | 2018146690 | A1 | 8/2018 |
| WO | 2018150314 | A1 | 8/2018 |
| WO | 2018156930 | A1 | 8/2018 |
| WO | 2018187582 | A1 | 10/2018 |
| WO | 2018220143 | A1 | 12/2018 |
| WO | 2018220146 | A1 | 12/2018 |
| WO | 2019050831 | A1 | 3/2019 |
| WO | 2019051007 | A1 | 3/2019 |
| WO | 2019051108 | A1 | 3/2019 |
| WO | 2019051007 | A8 | 4/2019 |
| WO | 2019063521 | A1 | 4/2019 |
| WO | 2019079364 | A1 | 4/2019 |
| WO | 2019101855 | A1 | 5/2019 |
| WO | 2019232213 | A1 | 12/2019 |
| WO | 2020023839 | A1 | 1/2020 |
| WO | 2020121221 | A1 | 6/2020 |
| WO | 2020131247 | A1 | 6/2020 |
| WO | 2020132460 | A1 | 6/2020 |
| WO | 2020132668 | A2 | 6/2020 |
| WO | 2020132669 | A1 | 6/2020 |
| WO | 2020132670 | A1 | 6/2020 |
| WO | 2020132671 | A1 | 6/2020 |
| WO | 2020132678 | A1 | 6/2020 |
| WO | 2020144075 | A1 | 7/2020 |
| WO | 2020153765 | A2 | 7/2020 |
| WO | 2021094980 | A1 | 5/2021 |
| WO | 2021217055 | A1 | 10/2021 |
| WO | 2021236756 | A1 | 11/2021 |
| WO | 2022055920 | A1 | 3/2022 |
| WO | 2022167382 | A1 | 8/2022 |
| WO | 2023170632 | A1 | 9/2023 |

OTHER PUBLICATIONS

International Search Report and Written Opinion dated Mar. 3, 2020, in connection with PCT/US2019/066589 filed Dec. 16, 2019.

Extended European Search Report dated Jul. 3, 2020, in connection with EP20163433.4.

Extended European Search Report dated Sep. 16, 2020, in connection with EP Application No. 20178613.4, filed Nov. 29, 2017.

Wang et al., "Internal jugular vein ultrasound for the diagnosis of hypovolemia and hypervolemia in acutely ill adults; a systematic review and meta-analysis"; Internal and Emergency Medicine (2022) 17:1521-1532, Feb. 27, 2022.

Nippa et al., "Pulse wave velocity in human veins"; Journal of Applied Physiology, vol. 30, No. 4, Apr. 1971.

Rudski et al., Guidelines for the Echocardiographic Assessment of the Right Heart in Adults: A Report from the American Society of Echocardiography (J Am Soc Echocard 2010, 23: 685-713).

Stergiopulos et al. "Simple and accurate way for estimating total and segmental arterial compliance: The pulse pressure method" Ann Biomed Eng 22, 392-397 (1994).

Lee et al., "Prognostic significance of dilated inferior vena cava in advanced decompensated heart failure" International Journal of Cardiovascular Imaging (2014) 30:1289-1295.

Sonoo T, et al., "Prospective analysis of cardiac collapsibility of inferior vena cava using ultrasonography", J Crit Care 2015, http://dx.doi.org/10.1016/j.jcrc.2015.04.124.

Marik, et al., Does Central Venous Pressure Predict Fluid Responsiveness?*: A Systematic Review of the Literature and the Tale of Seven Mares, Chest (2008) 134(1):172-178.

Blehar, et al., Inferior vena cava displacement during respirophasic ultrasound imaging, Critical Ultrasound Journal (2012) 4:18.

Huguet et al., Three-Dimensional Inferior Vena Cava for Assessing Central Venous Pressure in Patients with Cardiogenic Shock, J Am Soc Echocardiogr. 2018; 31: 1034-43 (https://doi.org/10.1016/ j.echo. 2018.04.003).

Katzarski et al. "A Critical Evaluation of Ultrasound Measurement of Inferior Vena Cava Diameter in Assessing Dry Weight in Normotensive and Hypertensive Hemodialysis Patients," AJKD, vol. 30, No. 4, Oct. 1997, pp. 459-465.

Hellevik et al. Heart Vessels v13, No. 4, p. 175-180, Jul. 1998.

(56) References Cited

OTHER PUBLICATIONS

Minten et. al. Cardiovasc. Res, vol. 17, No. 10, pp. 627-632, Oct. 1983.

Dehkordi et al., Extracting Instantaneous Respiratory Rate From Multiple Photoplethysmogram Respiratory-Induced Variations; Frontiers in Physiology, vol. 9,Article 948; Jul. 18, 2018 (DOI: 10.3389/fphys.2018.00948).

Yates PhD dissertation, Stanford CA, SUDAAR 393 1969.

Miles et al "Peripheral Intravenous Volume Analysis (PIVA) for Quantitating Volume Overload in Patients Hospitalized With Acute Decompensated Heart Failure—A Pilot Study"; Journal of Cardiac Failure; 2018; https://doi.org/10.1016/j.cardfail.2018.05.003.

Reymond et al., Validation of a one-dimensional model of the systemic arterial tree Proceedings of the ASME 2009 Summer Bioengineering Conference (SBC2009); SBC2009-206424.

Peters et al.; Inductance calculation of planar multi-layer and multi-wire coils: An analytical approach, Sensors and Actuators A, 145-146, p. 394-404 (Year: 2007).

Horizon Scanning Research & Intelligence Centre; Furosemide sc2Wear micro-pump patch for oedema in heart failure National Institute for Health Research; NIHR HSRIC ID: 11808; Mar. 2016; pp. 1-10; www.hsric.nihr.ac.uk.

ISR Report and Written Opinion dated Dec. 30, 2020, in connection with PCT/EP2020/067713 filed on Jun. 24, 2020.

International Search Report and Written Opinion dated Mar. 27, 2018, in connection with PCT/US2017/063749.

International Search Report and Written Opinion dated Aug. 29, 2018, in connection with PCT/EP2018/064386.

International Search Report and Written Opinion dated Aug. 21, 2018, in connection with PCT/EP2018/064383.

International Search Report and Written Opinion dated Sep. 5, 2023, in connection with PCT/IB2023/055245, filed on May 22, 2023.

International Search Report and Written Opinion dated Feb. 18, 2021, in connection with PCT/EP2020/060669, filed Nov. 12, 2020.

International Search Report and Written Opinion dated Jan. 19, 2021, in connection with PCT/IB2020/079939, filed Oct. 23, 2020.

International Search Report and Written Opinion dated Oct. 19, 2017, in connection with PCT/US2017/046204.

Brennan, J.M., "Handcarried Ultrasound Measurement of the Inferior Vena Cava for Assessment of Intravascular Volume Status in the Outpatient Hemodialysis Clinic"; Clinical Journal of the American Society of Nephrology; pp. 749-753; Jan. 23, 2006.

International Search Report and Written Opinion dated Oct. 20, 2016, in connection with PCT/US2016/045385 filed Aug. 3, 2016.

Voroneanu et al., "The relationship between chronic vol. overload 3 and elevated blood pressure in hemodialysis patients: 4 use of bioimpedance provides a different perspective 5 from echocardiography and biomarker methodologies," Int Urol Nephrol, 2010, Sep. 42(3):789-97.

Cannesson et al., "Respiratory Variations in Pulse Oximetry Plethysmographic Waveform Amplitude to Predict Fluid Responsiveness in the Operating Room," Anesthesiology 2007; 106:1105-11.

Abraham et al., "The Role of Implantable Hemodynamic Monitors to Manage Heart Failure," Heart Failure Clin 11 (2015) 183-189.

Tallaj et al., "Implantable Hemodynamic Monitors," Cardiol Clin 29 (2011) 289-299.

Tang et al., "Measuring impedance in congestive heart failure: Current options and clinical applications," American Heart Journal 157 (3) 402-411.

Merchant et al., "Implantable Sensors for Heart Failure," Circulation: Arrhythmia and Electrophysiology. 2010; 3:657-667.

Unadkat, Jignesh V., et al. "The Development of a Wireless Implantable Blood Flow Monitor," Ideas and Innovations, American Society of Plastic Surgeons, 136:199 (2015).

Steinhouse, David et al., "Implant Experience with an Implantable Hemodynamic Monitor for the Management of Symptomatic Heart Failure," PACE (Aug. 2005) vol. 28, pp. 747-753.

Braunschweig, Frieder et al. "Dynamic changes in right ventricular pressures during haemodialysis recorded with an Implantable haemodynamic monitor," Nephrol Dial Transplant (2006) 21:176-183.

Karamanoglu, Mustafa et al., "Estimation of cardiac output in patients with congestive heart failure by analysis of right ventricular pressure waveforms," BioMedical Engineering OnLine 2011, 10:36.

Spiliopoulos, Sotirios et la., "Beneficial aspects of real time flow measurements for the management of acute right ventricular heart failure following continuous flow ventricular assist device implantation," Journal of Cardiothoracic Surgery (2012) 7:119.

Sharma, Arjun D. et al., "Right Ventricular Pressure During Ventricular Arrhythmias in Humans: Potential Implications for Implantable Antitachycardia Devices," JACC vol. 15, No. 3, Mar. 1, 1990, pp. 648-655.

Kjellstrom, Barbo et al., "Changes in Right Ventricular Pressures Between Hemodialysis Sessions Recorded by an Implantable Hemodynamic Monitor," The American Journal of Cardiology, 2009, 103:119-123.

Zile, Michael R. et al., "Transition From Chronic Compensated to Acute Decompensated Heart Failure," Circulation, American Heart Association (2008) 118:1433-1441.

Plicchi, G. et al., "Pea I and Pea II Based Implantable Haemodynamic Monitor: Pre Clinical Studies in Sheep," Europace (2002) 4, 49-54.

Vanderheyden, Marc et al., "Continuous Monitoring of Intrathoracic Impedance and Right Ventricular Pressures in Patients With Heart Failure," Circulation Heart Failure (2010) 3:370-377.

Jacobs, Donald L. et al., "Bedside vena cava filter placement with intravascular ultrasound: A simple, accurate, single venous access method," Technical Note, Journal of Vascular Surgery, vol. 46, No. 6, pp. 1284-1286, Dec. 2007.

Muller, Laurent et al., "Respiratory variations of inferior vena cava diameter to predict fluid responsiveness in spontaneously breathing patients with acute circulatory failure: need for a cautious use," Critical Care 2012, 16:R188.

Blehar, David J. et al., "Identification of congestive heart failure via respiratory variation of inferior vena cava diameter." American Journal of Emergency Medicine (2009) 27, 71-75.

Miller, Joseph B., et al., "Inferior vena cava assessment in the bedside diagnosis of acute heart failure," American Journal of Emergency Medicine (2012) 30, 778-783.

Corl, Keith et al., "Bedside sonographic measurement of the inferior vena cava caval index is a poor predictor of fluid responsiveness in emergency department patients," Emergency Medicine Australasia (2012) 24, 534-539.

Feissel, et al. "The respiratory variation in inferior vena cava diameter as a guide to fluid therapy," Intensive Care Med (2004) 30: 1834-1837.

Nakao, Shoichiro et al., "Effects of Positional Changes on Inferior Vena Caval Size and Dynamics and Correlations with Right-Sided Cardiac Pressure," American Journal of Cardiology (1987; 59:125-132).

Saha, Narayan M., et al., "Outpatient Use of Focused Cardiac Ultrasound to Assess the Inferior Vena Cava in Patients With Heart Failure," American Journal of Cardiology (2015).

Ishizaki, et al. "Measurement of inferior vena cava diameter for evaluation of venous return in subjects on day 10 of a bed-rest experiment," J Appl Physical 96: 2179-2186, 2004.

Carbone et al. "Inferior Vena Cava Parameters Predict Re-admission in Ischaemic Heart Failure", European Journal of Clinical Investigations, 2014, 44(4): 341-349.

Bertram, C.D et al., "Cross-sectional area measurement in collapsed tubes using the transformer principle", Med. & Biol. Eng. & Comput, 1989, 27, 357-364.

Moreno, Augusto et al., "Mechanics of Distension of Dog Veins and Other Very Thin-Walled Tubular Structures", Circulation Research, vol. XXVII, Dec. 1970, pp. 1069-1080.

Tafur, Emilio et al., "Simultaneous Pressure, Flow and Diameter of the Vena Cava with Fright and Exercise", Circulation Research, vol. XIX, Jul. 1966., pp. 42-50.

Guntheroth, Warren G., et al., "Effect of Respiration on Venous Return and Stroke Volume in Cardiac Tamponade", Circulation Research, vol. XX, Apr. 1967, pp. 381-390.

(56) References Cited

OTHER PUBLICATIONS

Bartels, Lambertus et al., "Improved Lumen Visualization in Metallic Vascular Implants by Reducing RF Artifacts", Magnetic Resonance in Medicine 47:171-180 (2002).

Guntheroth, Warren G., "in Vivo Measurement of Dimensions of Veins with Implications Regarding Control of Venous Return", IEEE Transactions on Bio-Medical Engineering, Oct. 1969; pp. 247-253.

Kivelitz, Dietmar et al., "A Vascular Stent as an Active Component for Locally Enhanced Magnetic Resonance Imaging", Investigative Radiology, vol. 38, No. 3, 147-152 (2003).

Reddy, Reddy R.V., et al., "A Catheter-Tip Probe for Dynamic Cross-Section Area Measurement", pp. 149-158. (1973).

Stegall, H. Fred, "Survey of Dimension Transducers", Chronically Implanted Cardiovascular Instrumentation, pp. 107-115 (1973).

D. H. Bergel, "The Measurement of Lengths and Dimensions", Cardiovascular Fluid Dynamics, vol. 1. pp. 91-114 (1972).

Baan, Jan et al., "Dynamic Local Distensibility of Living Arteries and its relation to Wave Transmission", Biophysical Journal, vol. 14, (1974); pp. 343-362.

International Search Report and Written Opinion in connection with PCT/US2016/017902, dated Jul. 27, 2016.

Reems, Miryam et al., Central Venous Pressure: Principles, Measurement, and Interpretation, Vetlearn.com, Jan. 2012, Compendium: Continuing Education for Veterinarians, pp. E1-E10.

Yamauchi, Hideko et al., "Correlation Between Blood Volume and Pulmonary Artery Catheter Measurements", Department of Surgery and Surgical Critical Care, University of Hawaii, 2005.

Abraham, William T. et al., "Wireless pulmonary artery haemodynamic monitoring in chronic heart failure: a randomised controlled trial"; www.thelancet.com, vol. 377, Feb. 19, 2011, pp. 658-666.

Guiotto, Giovanna et al., "Inferior vena cava collapsibility to guide fluid removal in slow continuous ultrafiltration: a pilot study", Intensive Care Med (2010) 36:696-696.

Martens, Pieter et al., "Current Approach to Decongestive Therapy in Acute Heart Failure", Curr Heart Fail Rep (2015) 12:367-378.

Dupont, Matthias et a., "Impact of Systemic Venous Congestion in Heart Failure", Curr Heart Fail Rep (2011) 8:233-241.

Marik, Paul E. et al., "Hemodynamic parameters to guide fluid therapy", Annals of Intensive Care 2011, 1:1; http://www.annalsofintensivecare.com/content/1/1/1.

Silverberg, Donald et al., "The association between congestive heart failure and chronic renal disease", Curr Opin Nephrol Hypertens 13: 163-170, 2004.

International Search Report and Written Opinion dated Nov. 4, 2019, in connection with PCT/US2019/034657, filed May 30, 2019.

Karami et al., "Semi-Automatic Algorithms for Estimation and Tracking of AP-Diameter of the IVC in Ultrasound Images," (Jan. 9, 2019) J. Imaging 2019, 5(1), 12 (Year 2019).

Tchernodrinski et al., "Inferior vena cava diameter change after intravenous furosemide in patients diagnosed with acute decompensated heart failure: Inferior Vena Cava Diameter after Furosemide", Journal of Clinical Ultrasound, Vo. 43, No. 3, Jun. 4, 2014; pp. 187-193; XP093329764, US ISSN: 0091-2751, DOI: 10.1002/jcu. 22173.

Tuplin et al, "Influence of the Respiratory Cycle on Caudal Vena Cava Diameter Measured by Sonography in Healthy Foals: A Pilot Study", Journal of Veterminary Internal Medicine, vol. 31, No. 5, Aug. 1, 2017; pp. 1556-1562, XP093329771, US ISSN: 0891-6640, DOI: 10.111/jvim.14793.

* cited by examiner

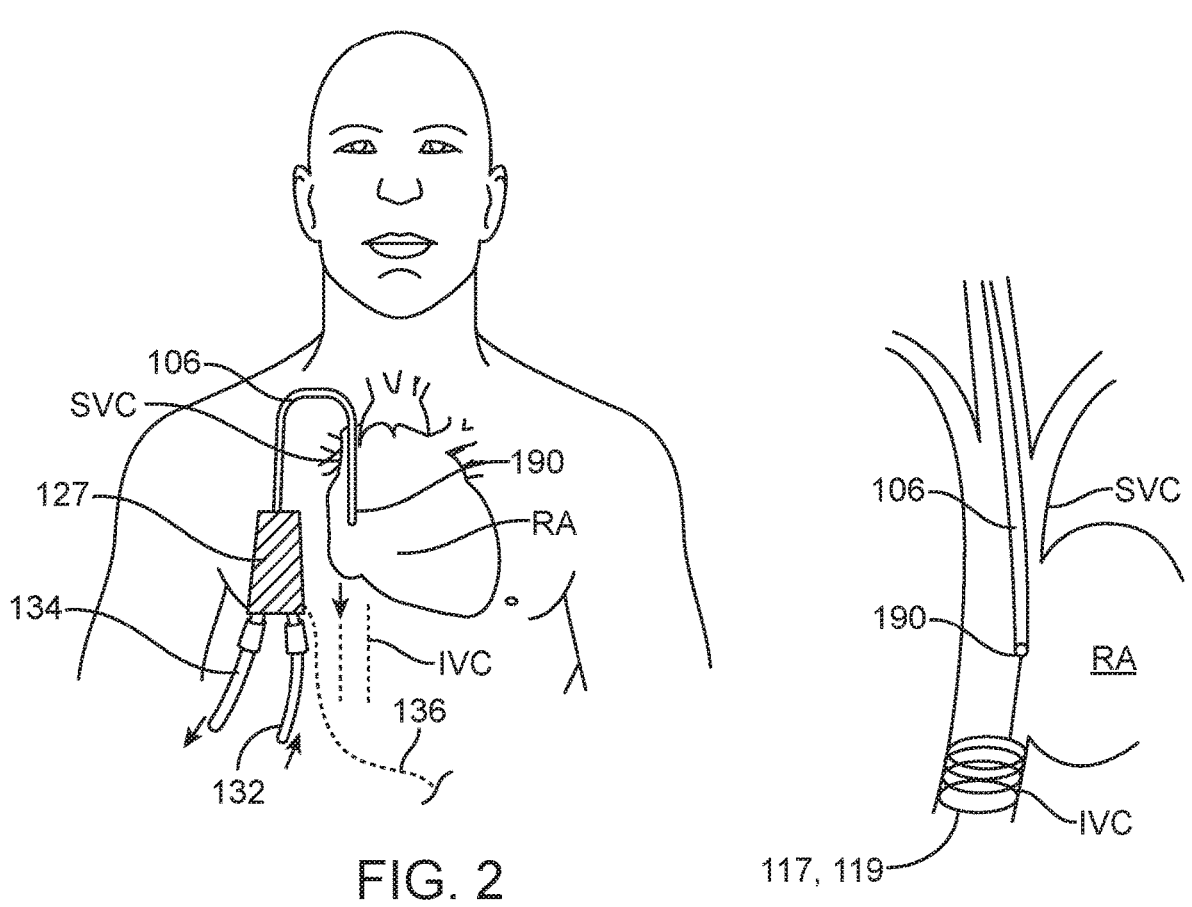
FIG. 2
FIG. 3B
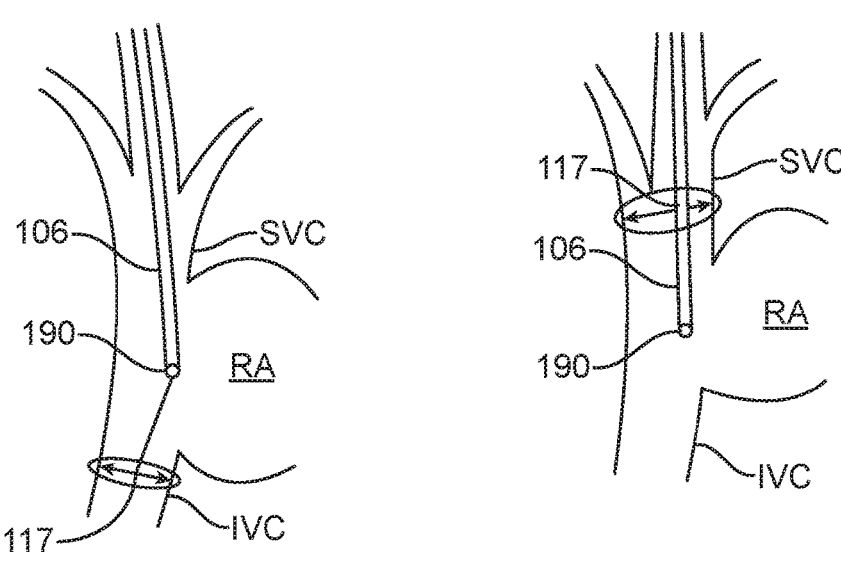
FIG. 3A                    FIG. 3C

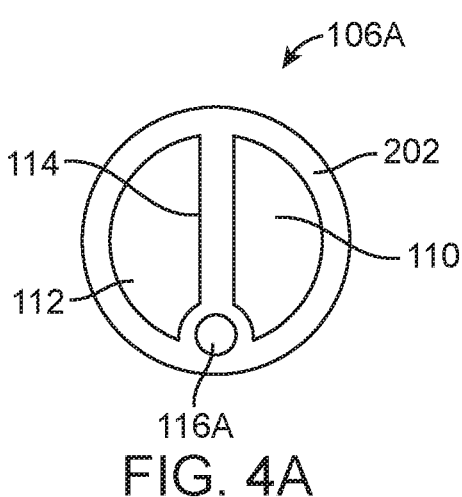
FIG. 4A
FIG. 4B
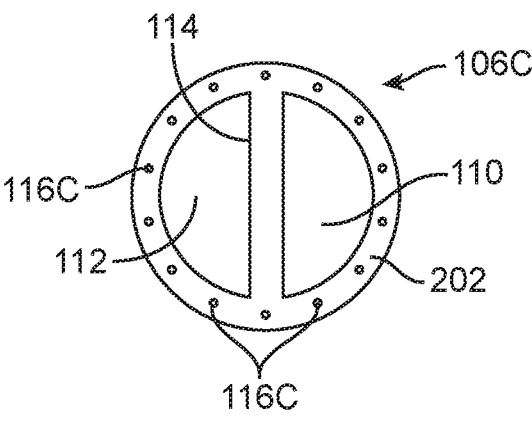
FIG. 4C
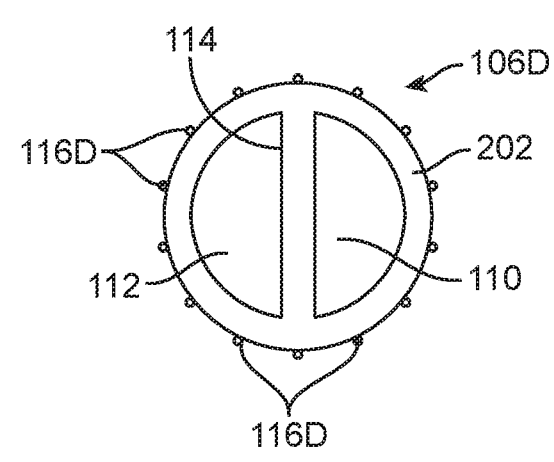
FIG. 4D
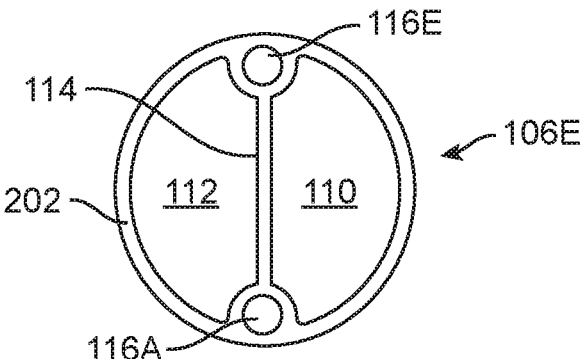
FIG. 4E

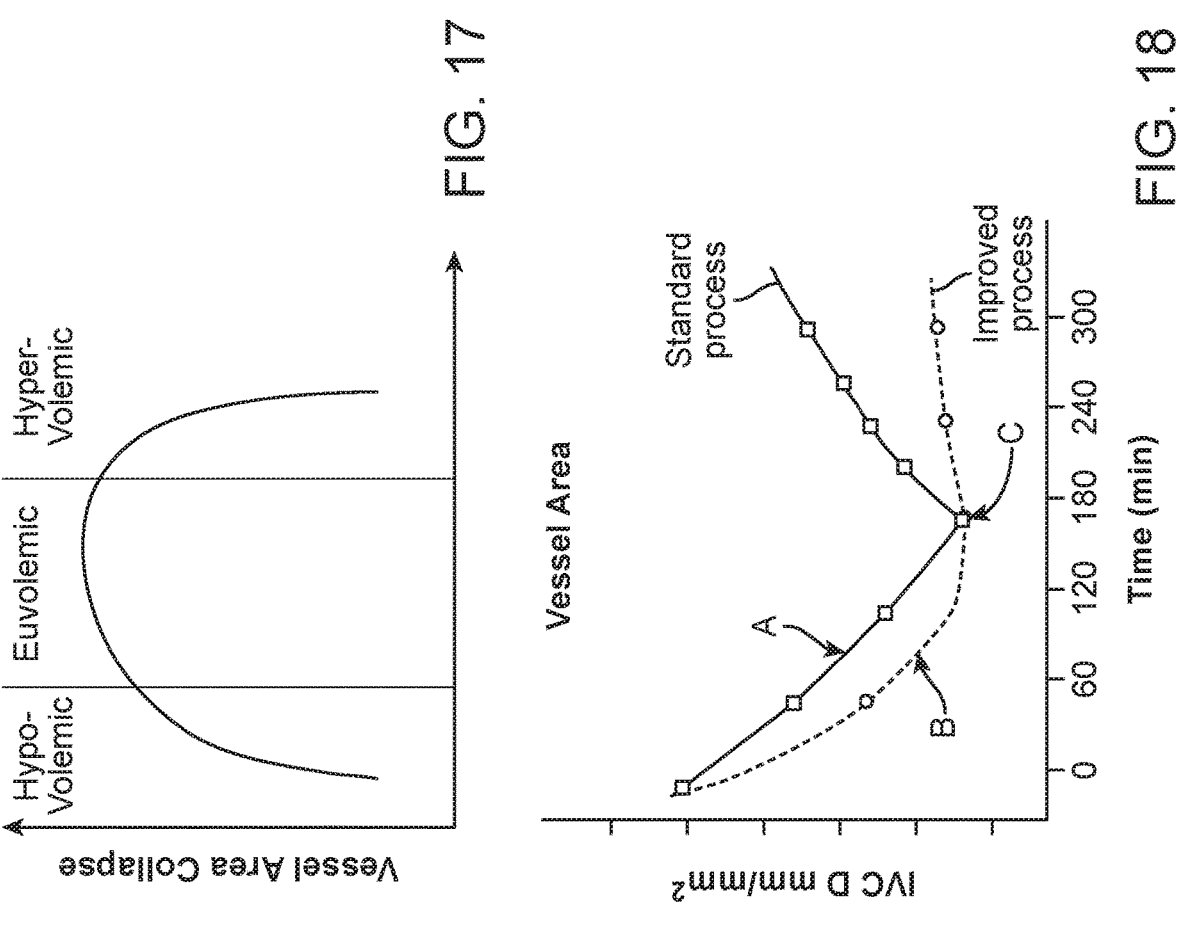
FIG. 17
FIG. 18
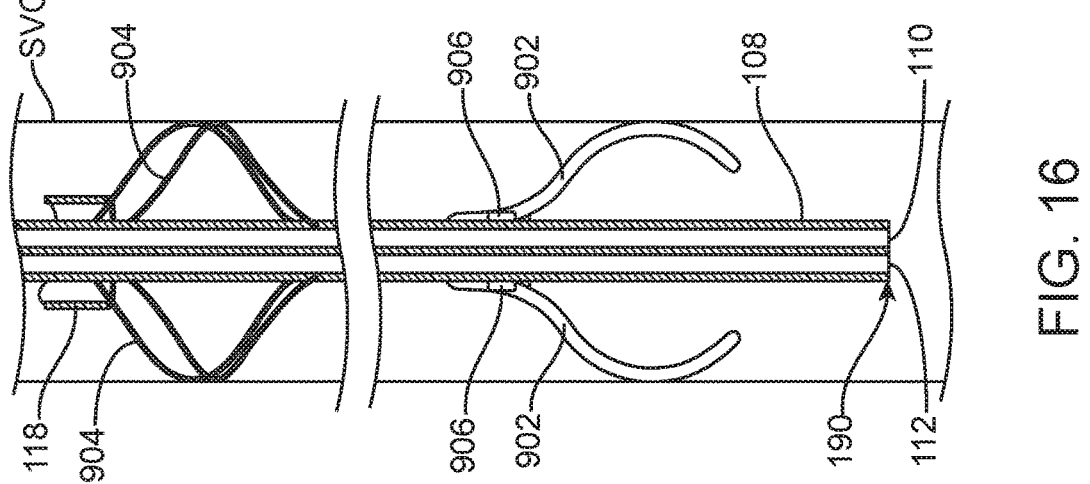
FIG. 16

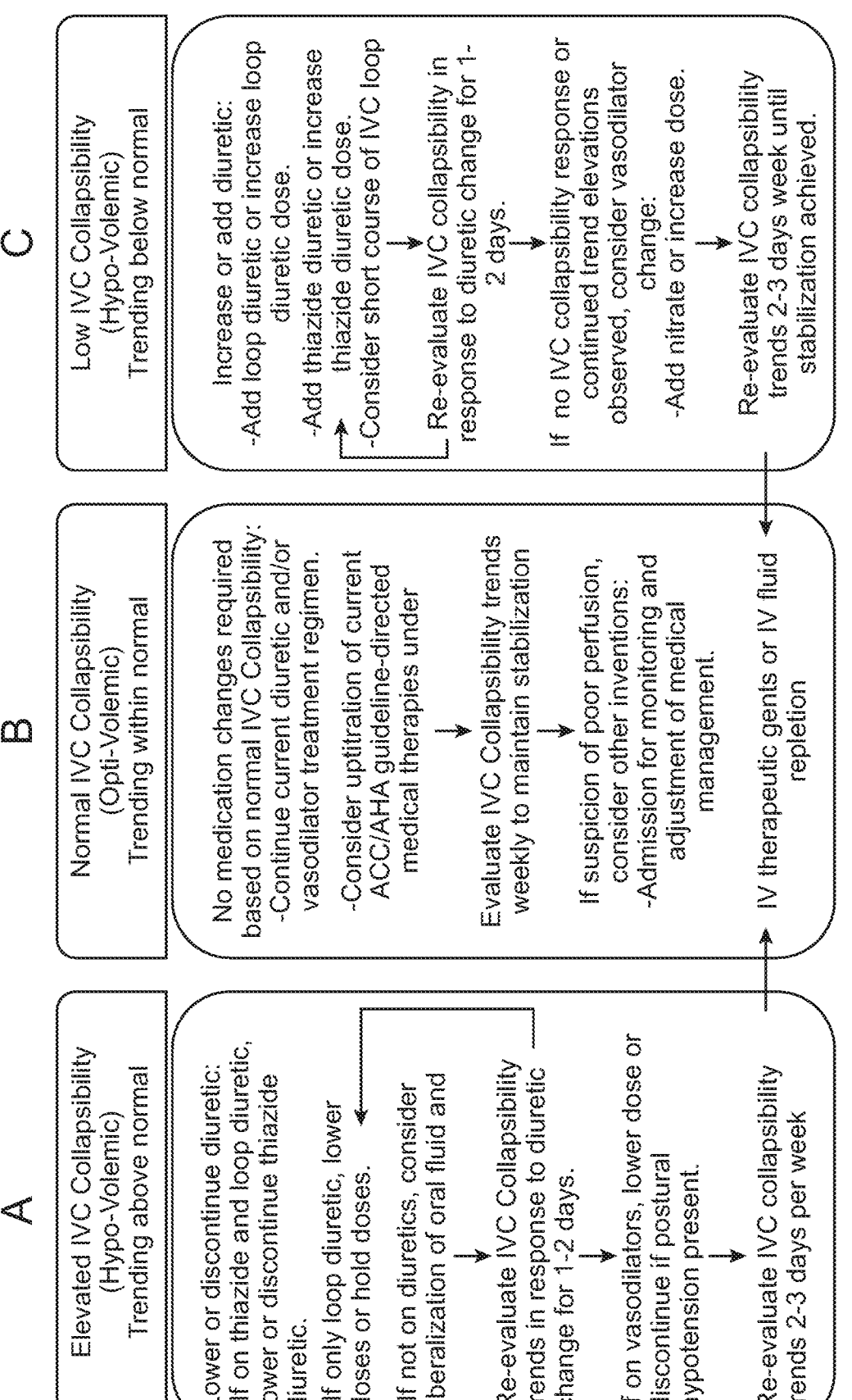

A

Elevated IVC Collapsibility (Hypo-Volemic) Trending above normal

Lower or discontinue diuretic:
-If on thiazide and loop diuretic, lower or discontinue thiazide diuretic.
-If only loop diuretic, lower doses or hold doses.
-If not on diuretics, consider liberalization of oral fluid and Re-evaluate IVC Collapsibility trends in response to diuretic change for 1-2 days.

If on vasodilators, lower dose or discontinue if postural hypotension present.

Re-evaluate IVC collapsibility trends 2-3 days per week

B

Normal IVC Collapsibility (Opti-Volemic) Trending within normal

No medication changes required based on normal IVC Collapsibility:
-Continue current diuretic and/or vasodilator treatment regimen.
-Consider uptitration of current ACC/AHA guideline-directed medical therapies under Evaluate IVC Collapsibility trends weekly to maintain stabilization If suspicion of poor perfusion, consider other inventions:
-Admission for monitoring and adjustment of medical management.

IV therapeutic gents or IV fluid repletion

C

Low IVC Collapsibility (Hypo-Volemic) Trending below normal

Increase or add diuretic:
-Add loop diuretic or increase loop diuretic dose.
-Add thiazide diuretic or increase thiazide diuretic dose.
-Consider short course of IVC loop Re-evaluate IVC collapsibility in response to diuretic change for 1-2 days.

If no IVC collapsibility response or continued trend elevations observed, consider vasodilator change:
-Add nitrate or increase dose.

Re-evaluate IVC collapsibility trends 2-3 days week until stabilization achieved.

1036 — Display

1024

Storage Device

1028 — Medium

1020 — Instructions

1052

Display Adapter

1032

Input Device

1012

1020

Instructions

Processor

1004

Peripheral Interface(s)

1056

1016

Input/ Output System

Instructions

Memory

1008

1020

Network Interface — 1040

1048 — Remote Device

Network

1044

DIALYSIS CATHETERS WITH INTEGRATED FLUID STATUS SENSING AND RELATED SYSTEMS AND METHODS

RELATED APPLICATIONS

The present application claims priority to U.S. Provisional Patent Application No. 62/778,657, filed on Dec. 12, 2018, and entitled "Diagnostic and Dialysis Catheter System and Method", which application is incorporated herein by reference.

FIELD OF THE DISCLOSURE

The present disclosure relates to hemodialysis systems and methods, and more particularly to dialysis catheters with integrated diagnostic sensors, systems and related methods.

BACKGROUND

Hemodialysis (frequently shortened to just "dialysis") is the process of extracting and purifying blood for patients whose kidneys are not functioning correctly. In hemodialysis, waste products such as urea and creatinine are removed from the blood using an extracorporeal filtering machine, i.e., a hemodialysis machine. Conventional dialysis is usually performed three to four times per week and usually takes in the region of 4 hours, during which around 500 ml of blood are extracted. Vascular access is obtained either via a fistula (a connection formed between the arterial and venous-AV fistula, circulation systems) or via an intravenous catheter. In the cases where a catheter is used, it is inserted into the patient's vein. The inner jugular vein is a common catheter access point due to ease of access and proximity to the heart.

The catheter is used to extract the blood and transport it to a dialysis machine where it is filtered and then returned, via the catheter to the patient. In some cases the dialysis catheter remains in the patient longer term and in some cases the catheter is removed at the end of a treatment session. During a treatment session, the patient's entire volume of blood, around 4-6 liters, circulates through the machine every 15 minutes or so.

A target of the dialysis treatment is to get a patient to an ideal "dry weight". This target "dry weight" is determined experimentally by the treating physician at the start of a patient's treatment regimen and often does not change. There is, at present, no direct way to measure the patient's dry weight as it changes during treatment using the dialysis system and catheter placed in the patient. Determination of the "dry weight" during treatment and the patient's fluid state relative to the target fluid state, usually involves performing dialysis on the patient until they have symptoms of hypovolemia, or a lack of fluid volume. These symptoms include cramping and dizziness and are not a pleasant experience for patients.

In extreme cases patients can experience a "hypo crash" where the symptoms become extreme. This can occur during any dialysis session and requires immediate medical intervention, namely the re-introduction of some fluids into the patient, thus undoing some of the benefits of the session.

External techniques exist for approximating patient fluid status apart from symptoms experienced during dialysis, however, the challenge is that to date these techniques typically involve use of an external ultrasound, or other external imaging techniques, such as CT or MRI, to remotely image the patient's vena cava and then extrapolate fluid status from dimensional changes in the vena cava as estimated in the images. Such techniques are operator and equipment dependent, and are inaccurate for measurement of venae cavae/veins; not suitable for use in seated patients during their dialysis session; and are not integrated with hemodynamic equipment.

The unmet need is a method by which to determine how much volume should be extracted for a specific patient during each dialysis session.

SUMMARY OF THE DISCLOSURE

In one implementation, the present disclosure is directed to a dialysis catheter that includes an elongate body with a proximal end configured to be manipulated outside a patient's body and a distal end configured to extend into the patient's vasculature, the distal end defining blood removal and return ports communicating with internal blood removal and return lumens extending through the elongate body to the proximal end; a sensing pathway disposed in or on the elongate body; and a sensor element configured to dynamically measure changes in a diameter or area of the vessel, the sensor element supported by the elongate body so as to be positioned in the SVC or IVC with the distal end blood removal and return ports positioned at a treatment location in the patient's vasculature, wherein the sensing pathway is configured to provide communication between the sensor element and the proximal end of the elongate body.

In another implementation, the present disclosure is directed to a dialysis catheter that includes a dual lumen catheter body formed by a peripheral wall divided by a central inner wall with a proximal end configured to be manipulated outside a patient's body and a distal end configured to extend into the patient's vasculature, the distal end defining blood removal and return ports communicating with internal blood removal and return lumens extending through the catheter body to the proximal end; a third lumen defined at least in part by the inner wall and extending from the distal end to the proximal end of the catheter body; a sensor catheter slidably disposed within and deployable from the third lumen; a sensor element disposed at the distal end of the sensor catheter, the sensor element configured to dynamically measure changes in a diameter or area of the vessel; a retractable deployment sheath disposed around the catheter body; one or more anchor means for anchoring at least one of the distal end of the catheter body or the sensor element at a desired location in the patient's vasculature; a catheter hub disposed at the proximal end of the catheter body, the catheter hub configured to provide connection and communication for the blood removal and return lumens and the third lumen with a therapy system; and a sheath hub disposed at the proximal end of the retractable deployment sheath, the sheath hub configured for actuation and manipulation of the sheath.

In yet another implementation, the present disclosure is directed to a method of hemodialysis that includes positioning a dialysis catheter within a patient's vasculature with a distal end of the dialysis catheter positioned at a blood withdrawal and return location, the dialysis catheter defining blood withdrawal and return lumens communicating with a dialysis system; delivering a vascular dimension sensor via the dialysis catheter into the patient's vasculature; dialyzing the patient through the catheter and dialysis system; monitoring a vascular dimension with the vascular dimension sensor during the dialyzing; determining changes in patient fluid state based on the monitored vascular dimension while performing the dialyzing; and controlling parameters of the dialyzing based on determined changes in patient fluid state.

In one embodiment, a catheter system may include a distally positioned lumen measurement means configured to measure a dimension of a vessel lumen in which it is placed; optional anchoring means disposed at the catheter distal end also may be included. The catheter system defines plural dialysis lumens for transfer of the blood between a patient and dialysis machine. In a further embodiment, the catheter system so configured may cooperate with a measurement control system. The measurement control system may be configured to generate, receive and/or process a measurement signal received from the lumen measurement means. The control system also may be connected to a dialysis machine via a wired or wireless connection to control or modulate therapy delivered thereby.

In another embodiment, a diagnostic and therapeutic system for treating a patient may include a catheter configured to measure at least one dimension of a vessel lumen and deliver a therapy into the vessel. The system also may include at least one control module configured to receive a signal indicative of the vessel lumen diameter from the catheter. A therapeutic device may be configured to receive the signal or an indicator thereof and to deliver a therapy to the patient via the catheter at least in part based upon information provided by the signal or indicator thereof.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 2 is a diagram illustrating placement of a diagnostic and dialysis catheter in the vasculature of a patient.

FIGS. 3A, 3B and 3C schematically illustrate locations for sensor measurements in alternative embodiments of the present disclosure.

FIGS. 4A, 4B, 4C, 4D, and 4E are schematic cross-sections of different catheter embodiments.

4

FIG. 16 schematically illustrates a further alternative catheter embodiment employing an SVC sensor and SVC anchor.

FIG. 17 is a plot of vessel area collapse versus vessel area (collapsibility curve) for the IVC.

FIG. 18 is a plot of IVC dimension (mm/mm2) over time comparing standard dialysis technique with improved technique disclosed herein.

Figure 19:
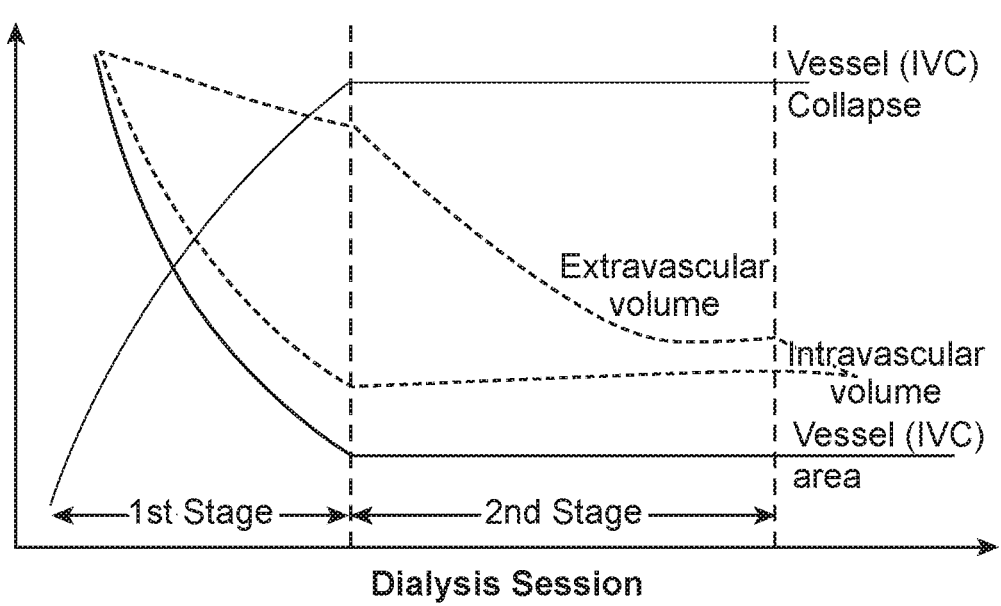

FIG. 19 is a plot showing relative changes in vessel area, vessel collapse, extravascular fluid volume and intravascular fluid volume over the course of a two-stage dialysis treatment procedure as disclosed herein.

Figure 20:
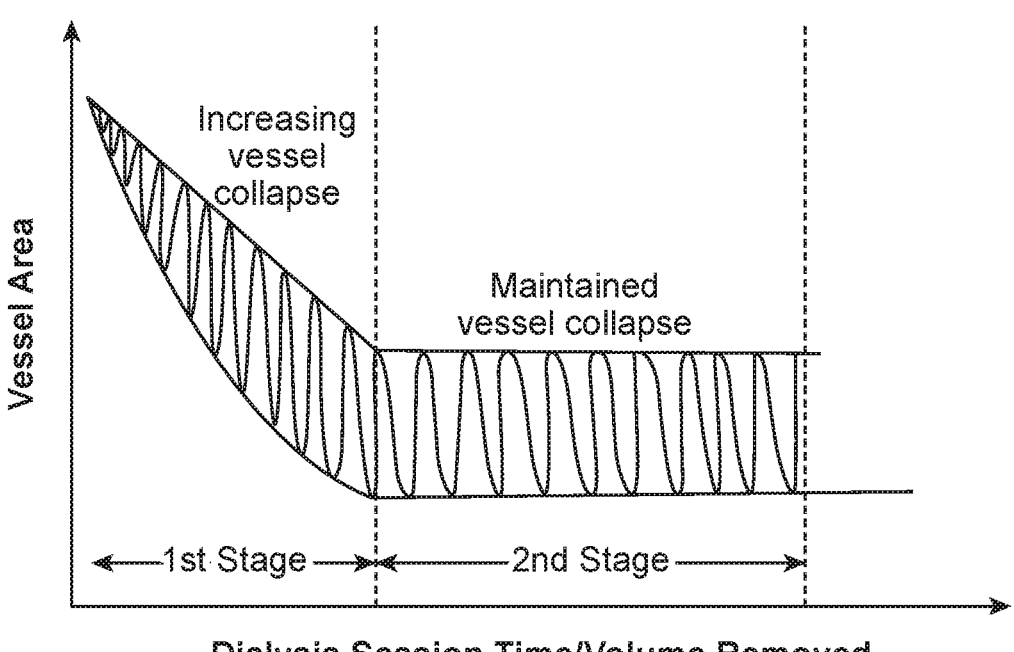

FIG. 20 is a plot showing changes in vessel area over dialysis session time for a two-stage dialysis treatment procedure as disclosed herein wherein the area between the upper and lower curves represents the variability in IVC area with each respiration.

Figure 21A:
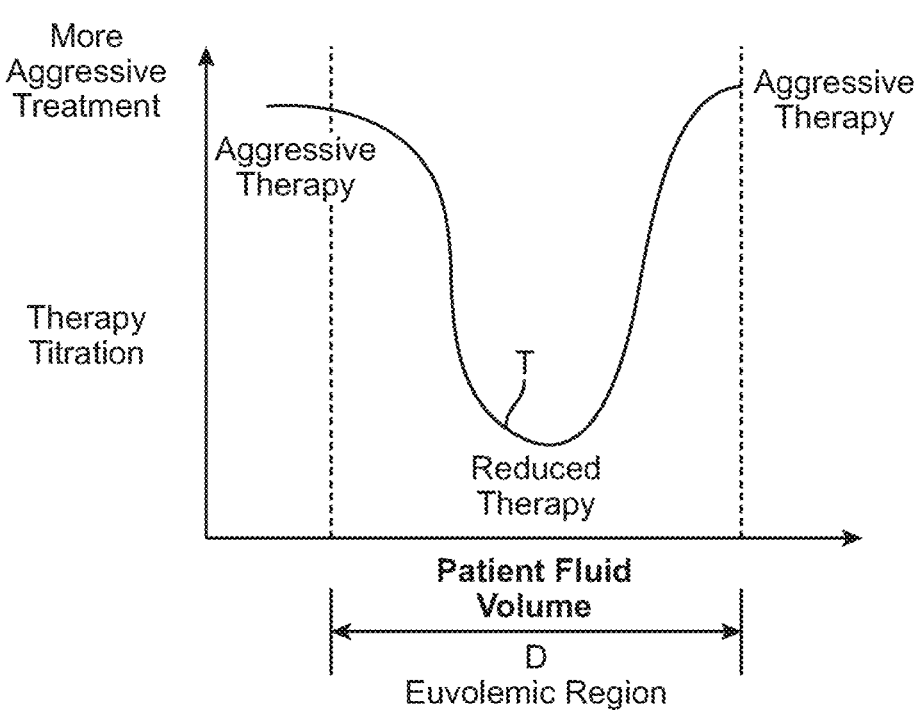
Figure 21B:
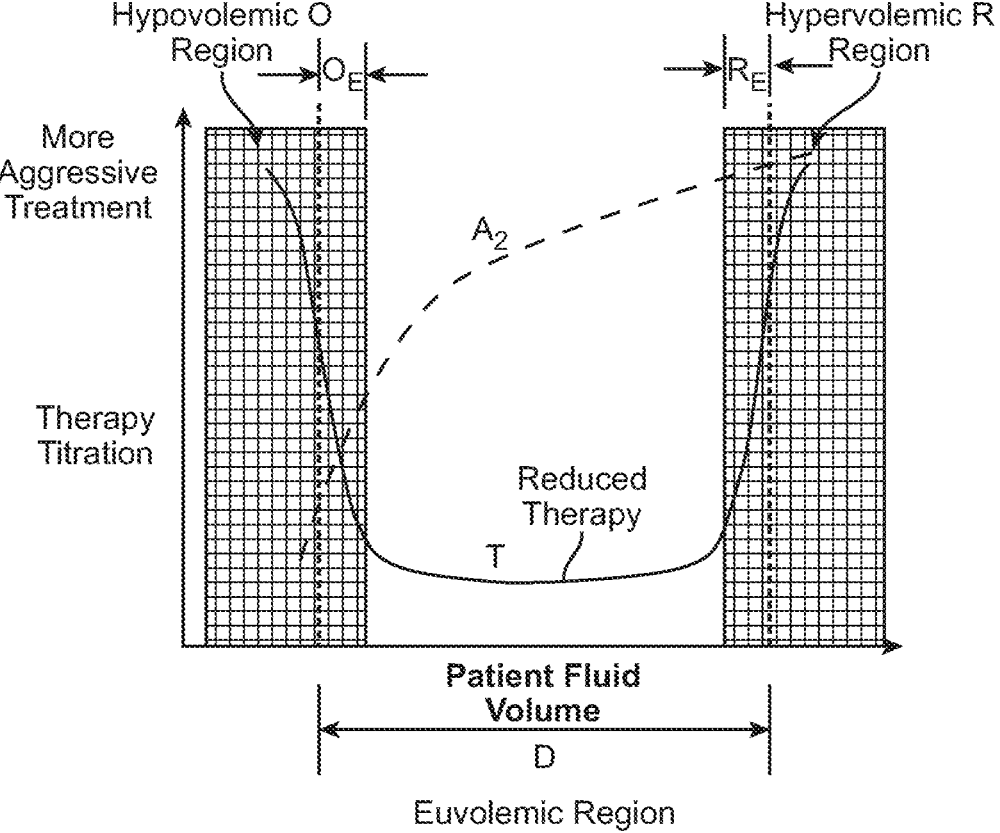

FIGS. 21A and 21B schematically illustrate alternative treatment embodiments employing titration of therapy using disclosed systems.

Figure 21C:
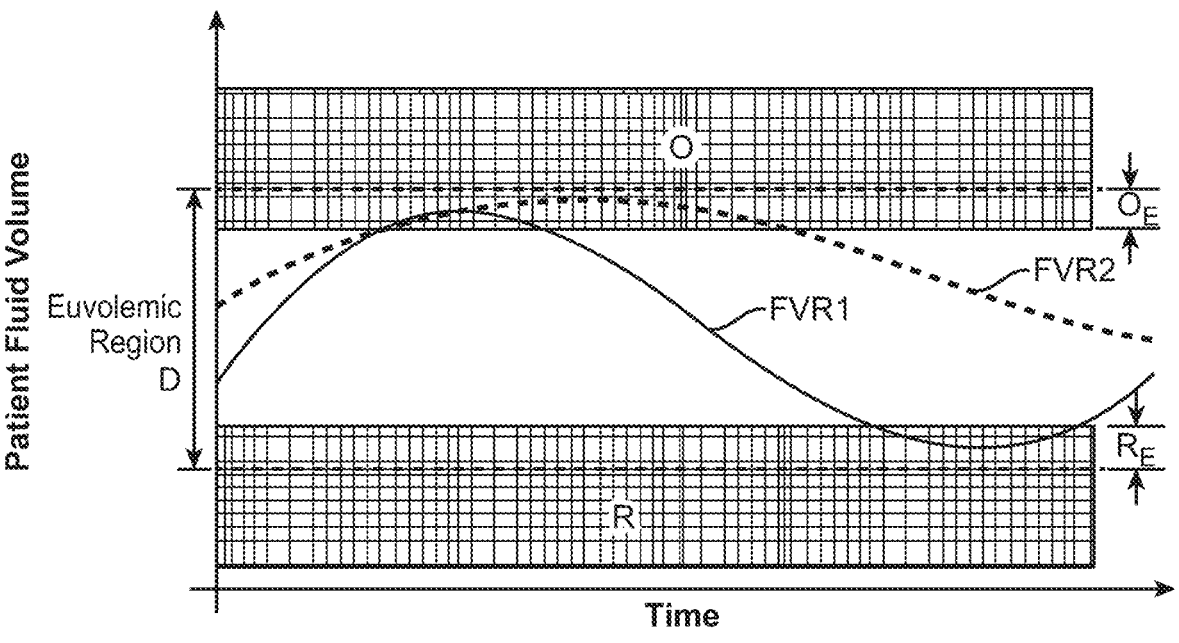
Figure 22A:
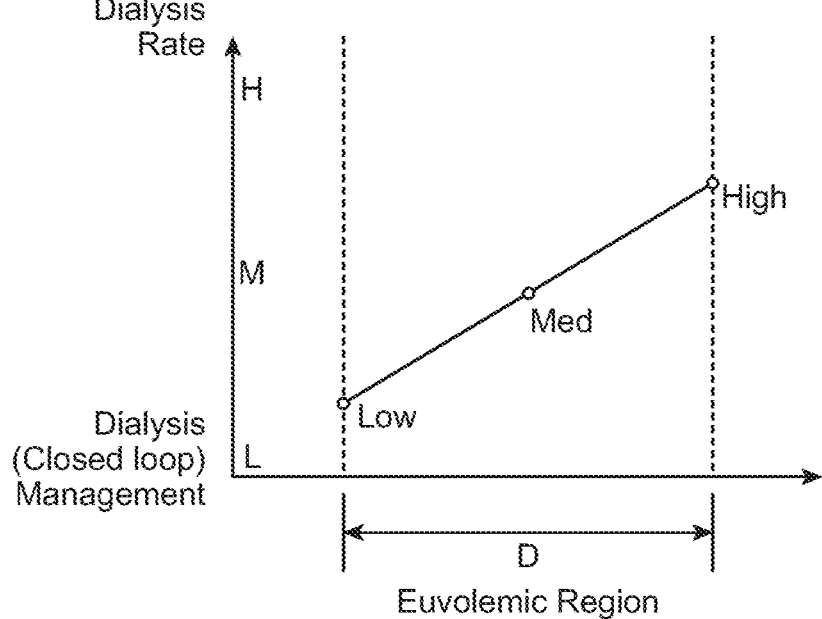
Figure 22B:
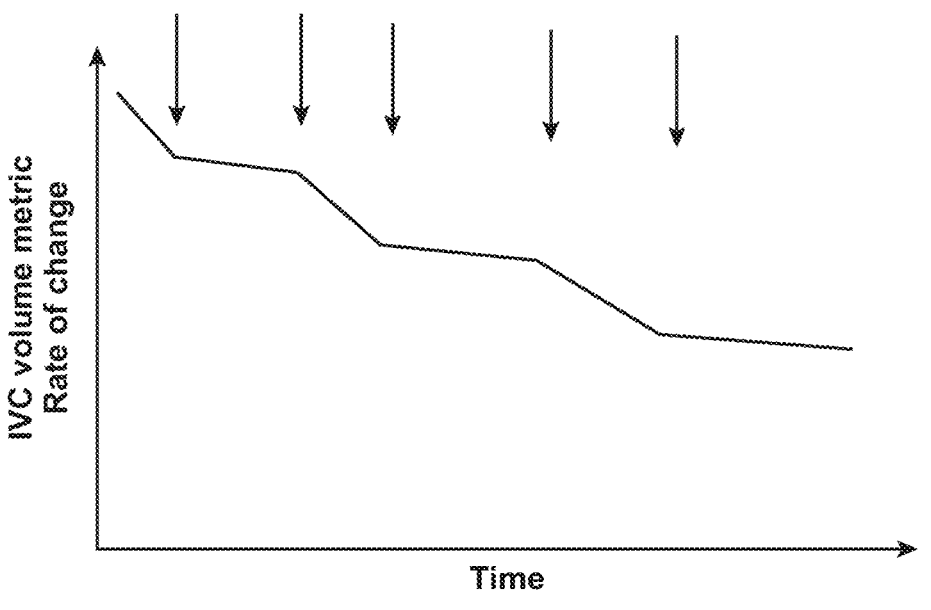
Figure 22C:
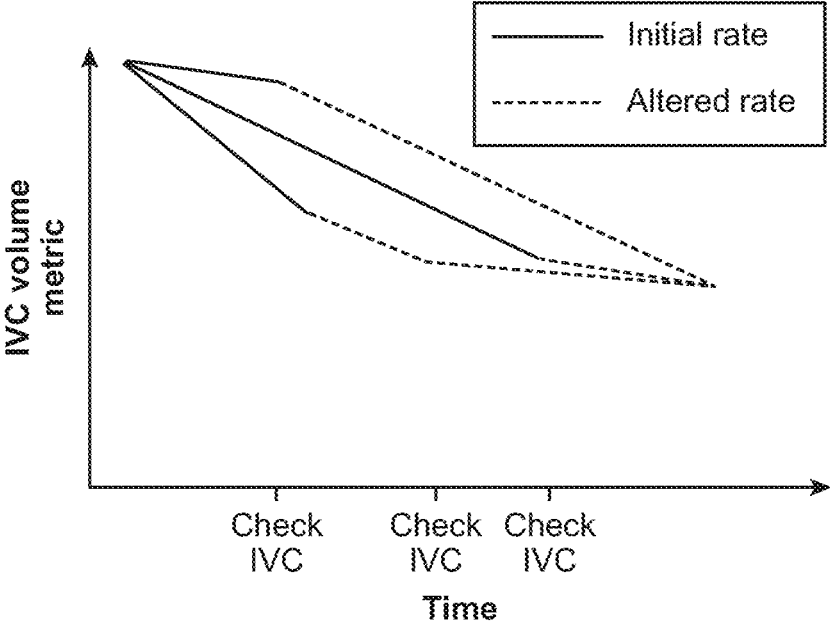
Figure 23A:
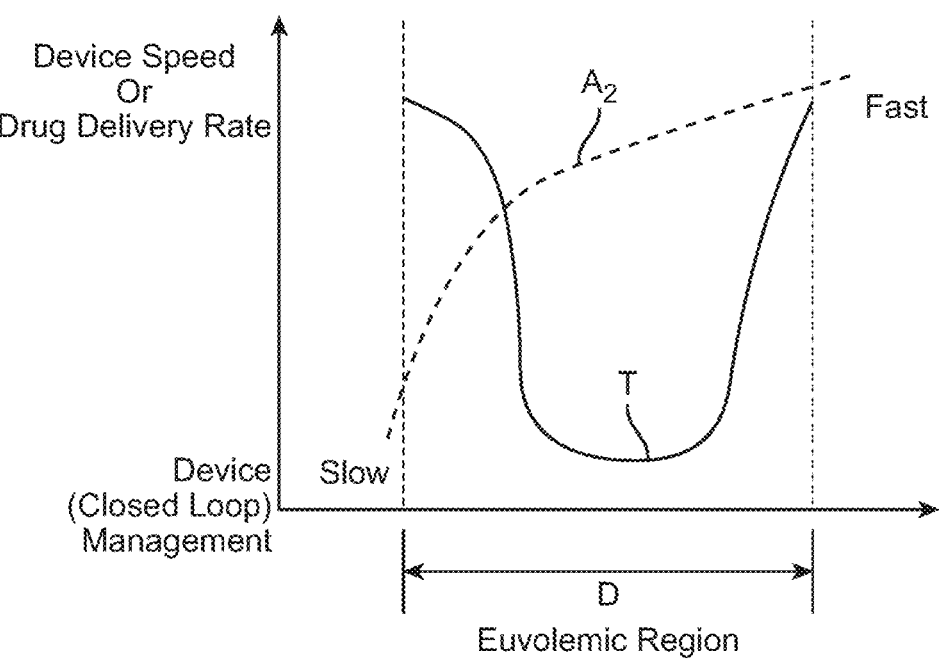
Figure 23B:
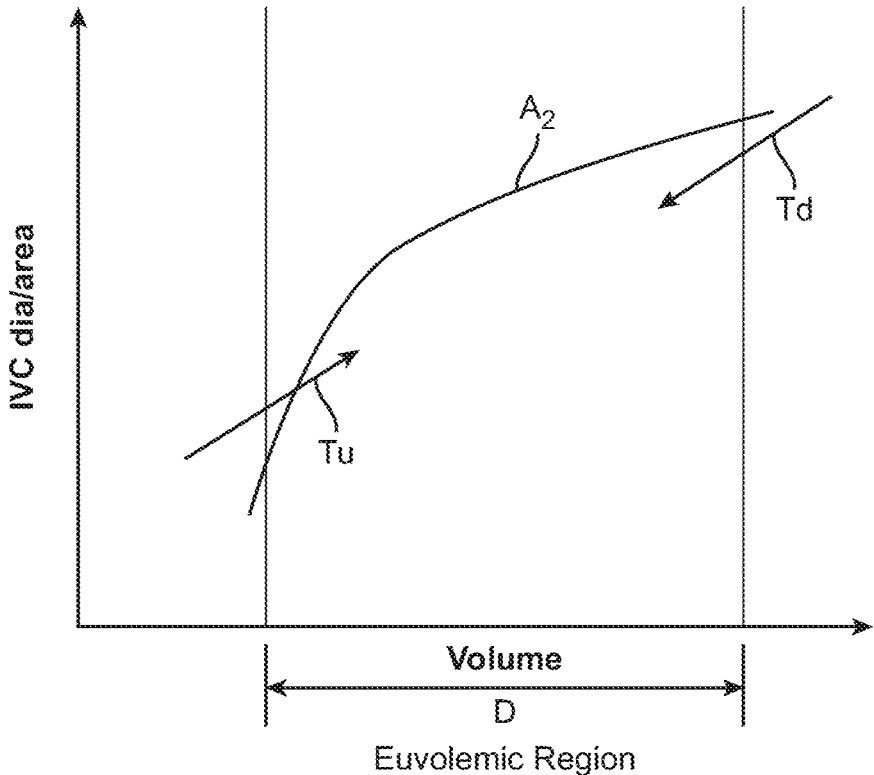

FIG. 21C illustrates a treatment scenario using disclosed systems.

FIGS. 22A, 22B, 22C, 23A and 23B schematically illustrate embodiments of closed loop control of dialysis and therapy/treatment devices using disclosed systems.

Figure 24:
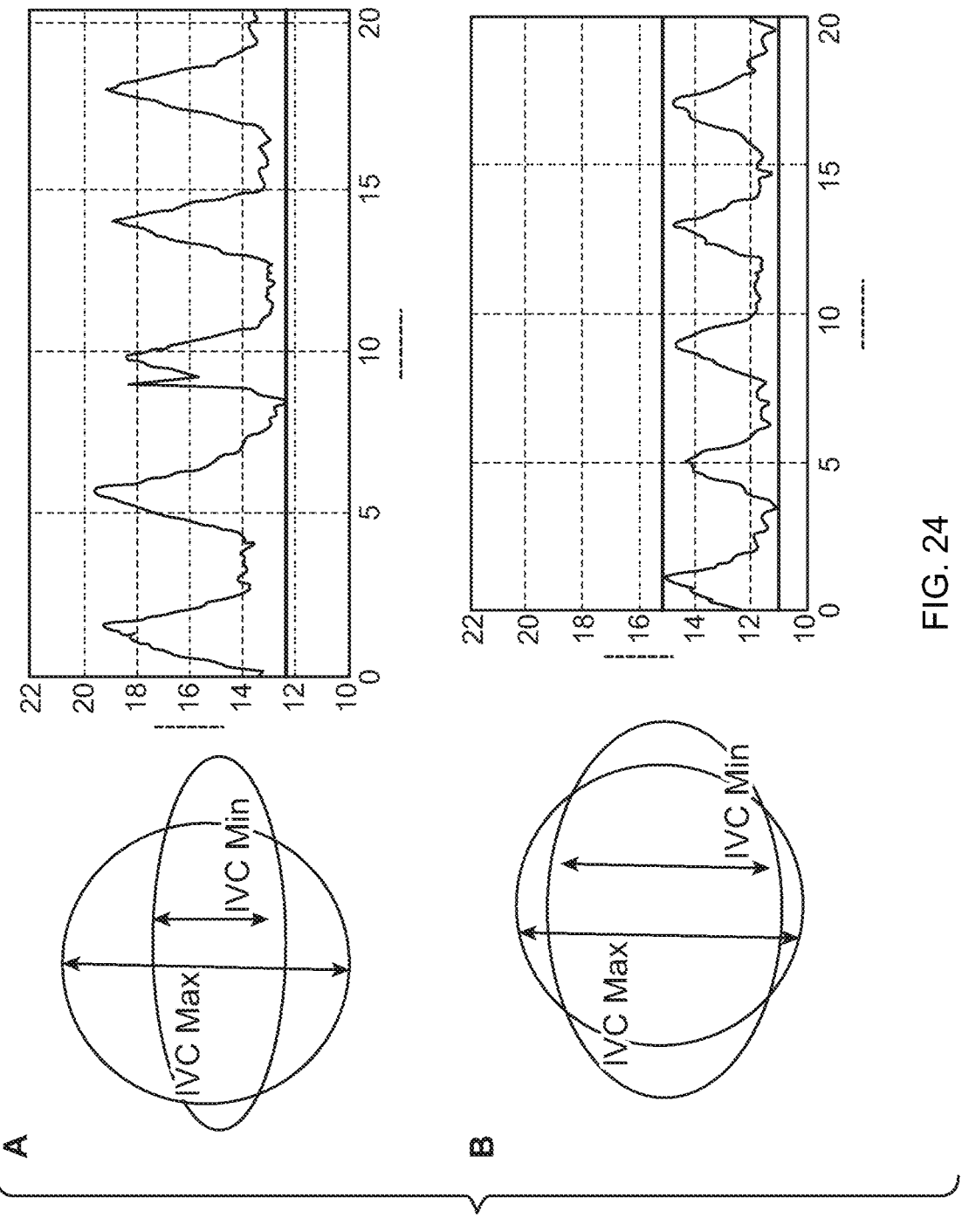

FIG. 24 illustrates an exemplary algorithm for determination of IVC collapsibility (IVC CI) on which a treatment algorithm may be based.

FIG. 25 illustrates a possible treatment algorithm according to the present disclosure.

Figure 26:

FIG. 26 is a block diagram of a computing system that can be used to implement any one or more of the methodologies disclosed herein and any one or more portions thereof.

DETAILED DESCRIPTION

Embodiments disclosed herein provide a closed-loop control hemodialysis treatment and diagnostic system in which a single catheter provides both treatment and diagnostic functions. Advantageously, a vascular dimension sensor is integrated with the dialysis catheter to maintain low profile shaft; maintain as large arterial and venous lumens as possible; maintain catheter flexibility; facilitate ease of use and integration with a hemodynamic system; and closed-loop connection between sensor system and hemodynamic system. The disclosed embodiments utilize the fact that the inferior and superior vena cava respond significantly to the addition and removal of blood volume from a patient and that response can be detected with appropriate sensors as described herein to generate a signal indicative of a vessel dimension and thus indicative of patient fluid state at the time of measurement.

Embodiments disclosed thus facilitate the monitoring of the vena cava during dialysis and provide additional, previously unavailable functionality incorporated into the dialysis catheter to measure the dimensions of the vena cava and thus deduce the fluid status relative to a patient's specific "dry weight" target. This functionality may be used, for example, to determine when to start and stop dialysis, but more significantly it can provide a closed-loop system including control of the hemodialysis system continuously, and in real or near-real time if desired, to make the treatment protocol truly patient specific, optimizing the filtration parameters to optimize for parameters such as speed or safety.

A principal feature of embodiments disclosed is thus integration of vascular dimension sensor(s) with the hemodialysis catheter, and in turn integration with hemodialysis system and sensor control. Features of the present disclosure and devices made in accordance therewith thus may include:

Dialysis lumens—for the transfer of the blood between the patient and dialysis machine.

Sensor element(s)—to sense vessel wall position and produce a signal indicative of a vessel dimension.

Sensor control system—generate, receive and process the sensor signal and may be connected to the dialysis machine via a wired or wireless connection.

Anchor(s) for catheter and/or sensor element—to hold the catheter and sensor element(s) in situ, may be located at the distal end of the catheter or further distally on an extended sensing element or further proximally on the catheter shaft, actuatable via mechanical means such as telescoping wires or retractable sheathes manipulable outside the body.

Disclosed embodiments permit direct, closed-loop feedback control of the hemodialysis treatment based on continuous current patient fluid status relative to a patient's "dry weight" to permit patient-specific optimization treatment. Advantages of such treatment optimization may include increased speed achieved by running the process fast when far from the dry weight and slowing as dry weight is approached, thus reducing overall dialysis time, getting patients drier, decreasing the fluid left in patients between dialysis sessions, thus improving clinical outcomes, and reducing negative symptoms associated with dialysis, i.e. cramping when too much fluid is removed from the patient. These and other advantages may be achieved by having more control on the fluid status via the venous measurement as is possible with disclosed embodiments.

Overall System Example

Figure 1:
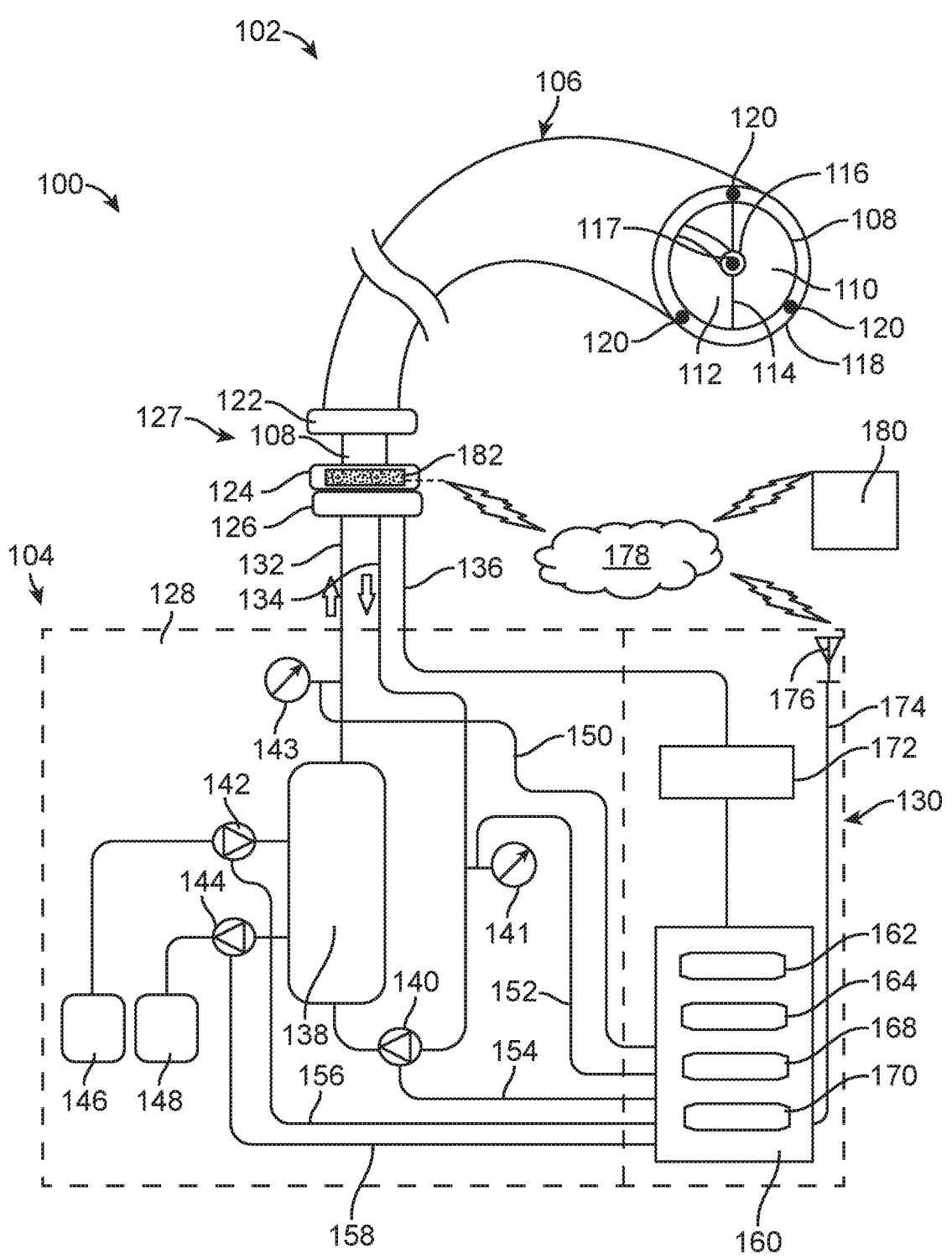
FIG. 1 is a schematic illustration of a complete diagnostic and dialysis catheter system with various alternatives according to embodiments disclosed herein.

FIG. 1 illustrates an example of one embodiment of a diagnostic and dialysis catheter system according to the present disclosure. System 100 generally includes catheter system 102 and control system 104. Turning first to catheter system 102, catheter 106 includes inner duel lumen catheter body 108 wherein lumens 110 and 112 are separated by inner wall 114. The duel lumen structure provides lumens for removing and returning blood in the same catheter structure. Sensing pathway 116, in this example a lumen provided in the center of inner wall 114, provides means for delivering and/or communicating with vascular sensor element 117. Sensor element 117 is configured to dynamically measure changes in the diameter or area of a vessel such as the IVC or SVC. Alternative catheter structures are described below, including sensor control and communication pathways that do not require a separate lumen (see FIGS. 4C and 4D) Also, further alternative sensor embodiments are discussed in more detail below (see FIGS. 5A-11 and 15).

Deployment sheath 118 surrounds catheter body 108. Deployment sheath 118 is moveable longitudinally relative to catheter body 108 to deploy or retract anchors 120, and/or in some embodiments additional or alternative sensor elements. Deployment sheath 118 is actuatable via deployment sheath hub 122, which may be retracted to cause anchors (or sensor elements) to extend outward to engage the vessel wall at a selected location. Note that depending on the type of anchor and deployment mechanism employed, deployment sheath 118 may or may not be used. Anchor embodiments and alternative actuation configurations are discussed in more detail below (see FIGS. 12-15 and 5C).

Sheath hub 122 along with catheter hub 124 and system-side connector 126 together form hub assembly 127 to provide fluid communication with dialysis module 128 of control system 104 via blood return and intake lines 132, 134. Connector 126 also optionally provides connection to data link 136 to permit sensor 117 in catheter 106 to communicate with diagnostic and control module 130.

Dialysis module 128 contains dialyzer 138, which may comprise a conventional dialyzer unit as known in the art. Blood flow into and out of dialyzer 138 is controlled by pump 140, which is in turn controlled by diagnostic and control module 130. Pumps 142 and 144 control flow of the fresh dialyzing solution 146 and used dialyzing solution 148 into and out of dialyzer 138, respectively. Blood supply and return pressure is monitored by pressure gauges 141, 143. Each of these pumps and pressure gauges has a data link (150, 152, 154, 156, 158) to diagnostic and control module 130.

Diagnostic and control module 130 includes control sub-module 160 including computing components such as processor 162, memory 164, storage 168 and user interface 170. Components of control-module 160 may be modified and configured specifically by persons of ordinary skill in order to accomplish functional control of system 100 as described herein. Sensor control sub-module 172 controls and interprets signals from sensor 117 in a manner appropriate for the specific sensor type, and communicates sensed information with control sub-module 160 in order to provide closed-loop feedback. In some embodiments, datalink 174 and antenna module 176 may be optionally provided to communicate wirelessly with network 178 and other network-enabled devices 180. It also may be desirable to provide direct wireless communication between the sensor and network 178, in which case wireless control module 182 may be provided, for example, in or with catheter hub 124 whereby data generated by sensor 117 may be directly wirelessly communicated. In general, any datalink described herein may be provided as a hardwired or wireless communication channel as is understood in the art.

A hemodialysis session is begun by placing dialysis catheter 106 in a large vein of the patient. Typically, catheter 106 is placed in the patient's superior vena cava (SVC) with distal tip 190 positioned in the right atrium (RA) as shown in FIG. 2. Access is commonly achieved via the internal jugular vein as also shown in FIG. 2, although other access sites are possible consistent with clinical conditions and standard dialysis practices. After confirmation of placement, which may utilize aspects of sensor functionality as below, hemodialysis proceeds with control of dialysis module 128 informed by the diagnostic and control module 130 in a closed-loop fashion based on information generated by sensor 117. Examples of such closed-loop control include altering blood flow through the dialyzer and/or concentration of the dialysate based on sensor measurements indicate the fluid status of the patient.

As discussed above, sensor element 117 is configured to provide a signal indicative of a dimension of a vessel, such as diameter, shape, area, collapsibility, for example, that may be correlated to the patient's fluid status. FIGS. 3A and 3B illustrate different sensing locations. In FIG. 3A vessel measurement with sensor element 117 is performed inferior to the heart, for example in the IVC. Sensing may be directly across the vessel or multidirectional, radially directed. Alternatively, as shown in FIG. 3B, sensing element 117 may be positioned superior to the heart, for example, in the SVC, jugular, brachial or similar vein. Once again, in this location sensing may be directly across the vessel or multidirectional, radially directed. Regardless of sensing location, distal tip 190 of catheter 106 remains positioned in the patient's right atrium (RA). Note that the embodiments of FIGS. 3A and 3B are not mutually exclusive and sensing may be done simultaneously or sequentially in more than one location with different catheter and sensor configurations as disclosed herein.

Catheter Configurations

Basic considerations in the structure and methods of making vascular catheters, including dual lumen dialysis catheters, are well-understood by persons of ordinary skill in the art. The present disclosure focuses specifically on structures uniquely suited for use in diagnostic and dialysis systems, and with other system components, as disclosed herein. FIGS. 4A-D illustrate examples of such structures. In particular, embodiments of dual lumen catheters made in accordance with the present disclosure typically will be provided with sufficient column stiffness to ensure that the distal portions are at a constant distance from the entry site into the vein. In use, the catheter is secured at the entry site and the column stiffness therefore helps to ensure the position of the distal elements (including the sensing elements). Because the catheter embodiments disclosed herein include additional sensing-related elements not found in conventional dual lumen dialysis catheters, the catheter body itself may be less stiff and rely on the presence of the sensing-related elements for a desired overall combined stiffness.

In the FIG. 4A embodiment, dual lumen catheter 106A includes peripheral catheter wall 202, which is divided by inner wall 114 to form venous and arterial blood lumens 110, 112, respectively. In this embodiment, sensing communication pathway 116A is provided as an eccentrically located longitudinal lumen for delivering and communicating with sensing devices as described herein below. Catheter 106B, shown in FIG. 4B, is substantially the same as catheter 106A, with the exception that sensing communication pathway 116B, again provided as a longitudinal lumen, is provided centrally rather than concentrically. A centrally located sensing pathway lumen may be chosen for sensors that utilize signal projection in multiple radial directions, whereas an excentric sensing communication pathway lumen will tend to place the sensor against one wall of the vessel so as to complement sensors that project signals non-radially.

In the embodiments of FIGS. 4C and 4D, wires are used as the sensing communication pathways instead of lumens. In catheter 106C, wires 116C are embedded in catheter wall 202 to provide communication and control for various sensor types as described herein. Alternatively, as in catheter 106D, wires 116D are attached on the outside of catheter wall 202 to provide communication and control for sensing elements.

Figures 7A, 7B, 7C:
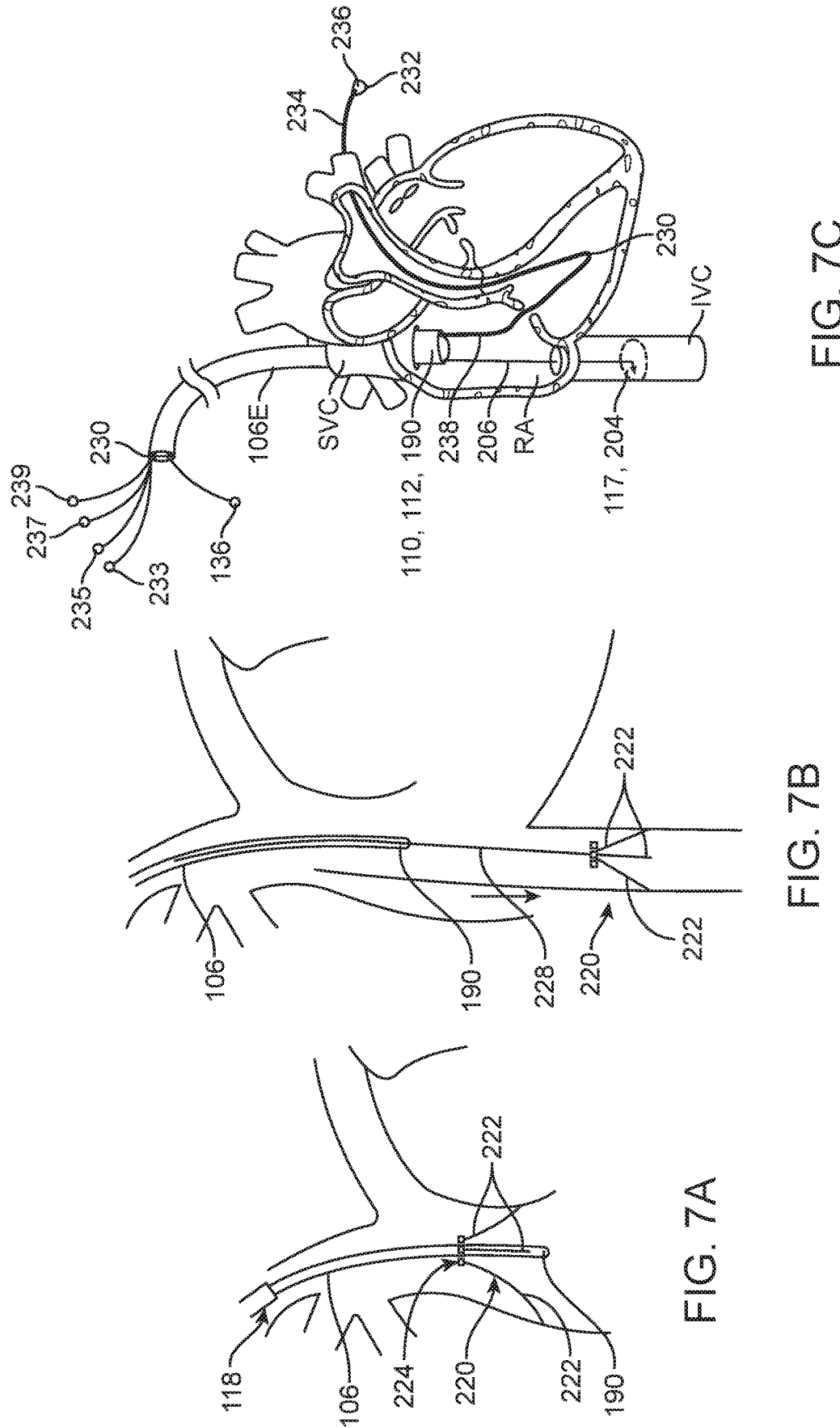
FIGS. 7A and 7B schematically illustrate alternative embodiments using strain gauge sensors.
FIG. 7C schematically illustrates a further alternative embodiment including a Swan-Ganz catheter.

In the embodiment illustrated in FIG. 4E, catheter 106E includes two excentric or edge-positioned communication pathways 116A and 116E, provided as longitudinal lumens. Lumen 116A may be used for delivering and communicating with sensing devices as described above, and lumen 116E may be used to deliver other devices, for example a Swan-Ganz catheter as illustrated in FIG. 7C. The cross-sectional arrangement of catheter 106E is otherwise substantially as described in prior embodiments, with venous and arterial blood lumens 110, 112, separated by inner wall 114 and surrounded by catheter wall 202.

Sensor Configurations

Numerous technical methods are available to persons of ordinary skill to be employed in sensor element 117 so as to provide a signal indicative of the desired vessel dimensions. Examples of such technical methods include:

Ultrasound—A piezo-electric element array of elements or other ultrasound transducer elements may be used as sensor element 117. Such sensors would be excited with an electrical charge to emit an ultrasound pulse. This pulse would be transmitted through the blood and reflected from the vessel wall, and detected by the piezo crystal where it would be converted back from mechanical to electrical energy. As the array is multiplexed, the returning signals can be used to generate a dimensional map of the vessel surrounding the catheter. Ultrasound sensor elements could be incorporated directly into catheter 106, at distal tip 190 and/or proximally for SVC measurement, or incorporated into a separate sensor device deployed further proximally via a lumen such as lumens 116A or 116B in FIGS. 4A and 4B.

Figure 4F:
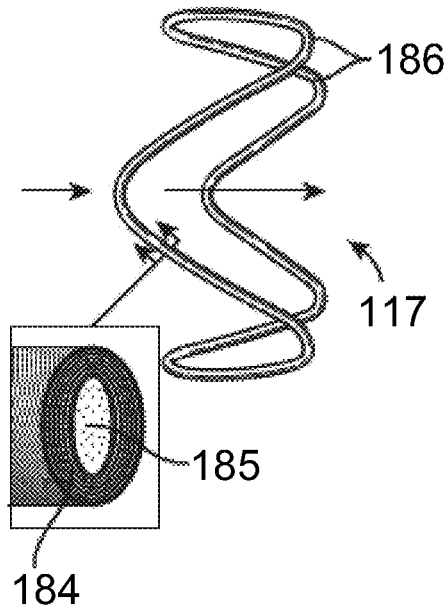
FIG. 4F schematically depicts an embodiment of a resonant circuit-based sensor according to the present disclosure.

Resonant circuit—An expandable coil may be incorporated into catheter 106 as sensor element 117, which would be expanded in order to make contact with the vessel wall. The coil would then be excited either directly and the impedance measured and used to determine vessel area, or could include a capacitor, forming a resonant circuit and be excited from externally and the resonant frequency be used to determine the vessel area. FIG. 4F illustrates an example of a such a resonant circuit sensor. The enlarged detail in the box of FIG. 4F represents a cross-sectional view taken as indicated. In this embodiment, sensor 117 includes multiple parallel strands of wire 184 formed around a frame 185. The frame is configured in a zig-zag shape with alternating crowns 186. With multiple strands of wires, the resonant circuit may be created with either the inclusion of a discrete capacitor, element or by the inherent inductance of the coils without the need for a separate capacitor as capacitance is provided between the wires 184 of the sensor. Note that in the cross-sectional view of FIG. 4F, individual ends of the very fine wires are not distinctly visible due to their small size. The wires are wrapped around frame 185 in such a way to give the appearance of layers in the drawing.

Light—Optical coherence tomography could be used to determine the vessel dimensions.

Impedance—A series of electrodes may be deployed as sensor element 117 via a nitinol structure to make contact with the vessel wall. Electrical charge could be passed between such electrodes in order to determine the vessel dimensions.

Balloon—A balloon provided as sensor element 117 could be inflated to make contact with the vessel wall. The balloon may include a lumen to avoid the occlusion of the vessel. This could then be used in a number of ways—the volume required to fill a non-compliant balloon could be used to determine area, an electrical charge could be passed between electrodes to determine the area (impedance planimetry).

Strain gauge—An expanding mechanical device equipped with a strain gauge may be used as sensor element 117 to determine at what point vessel wall contact is made and used to determine the vessel area.

Figure 5C:
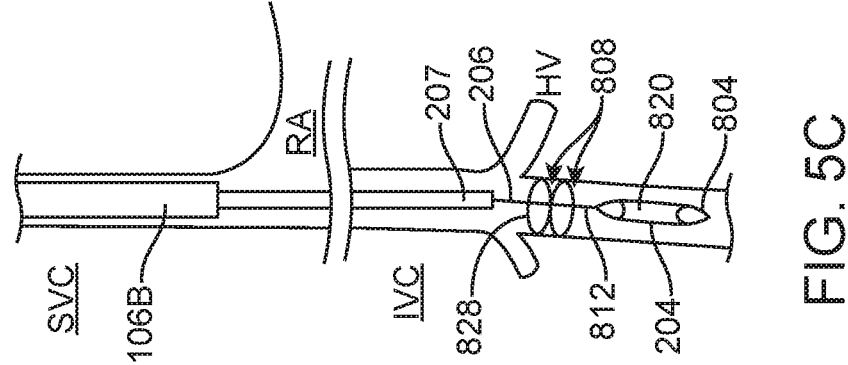
FIGS. 5A, 5B and 5C schematically illustrate alternative embodiments using ultrasound sensors.
Figure 5B:
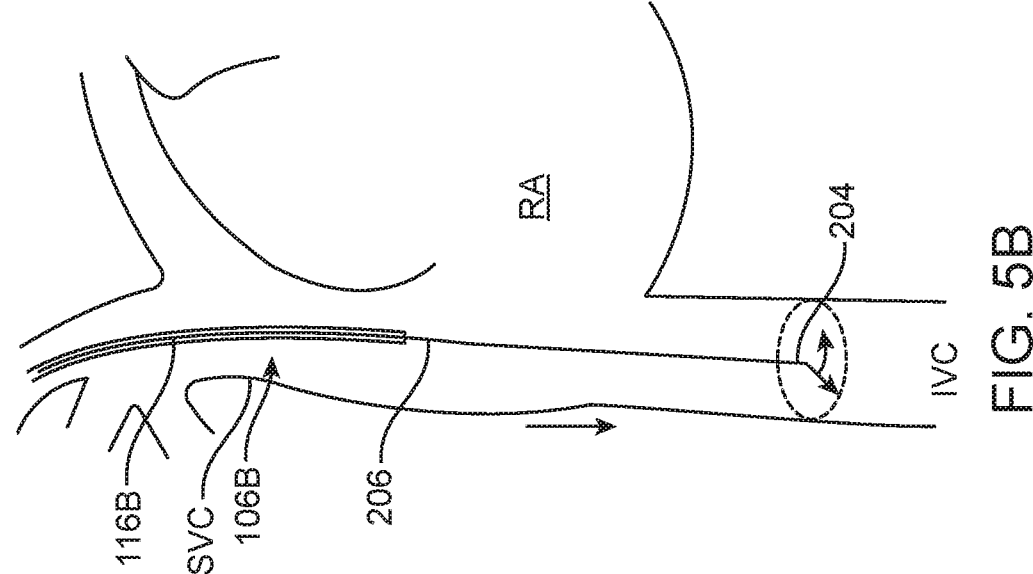
Figure 5A:
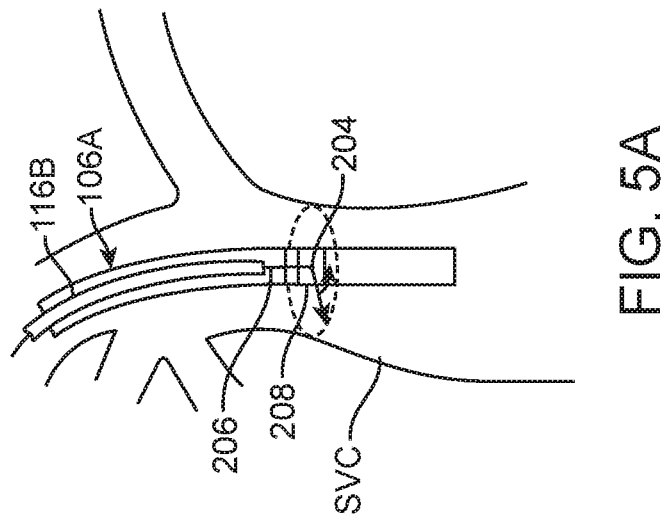

FIGS. 5A-C illustrate various alternative embodiments employing an ultrasound sensing element. In FIG. 5A, rotating ultrasound element 204 is deployed on the end of control wire 206. In this embodiment a catheter, such as catheter 106A, with central lumen 116B as the sensing communication pathway, may be used for deployment of ultrasound element 204 and control wire 206. Ultrasound element 204 may be a rotating ultrasound sensor that uses a 360 degree signal to determine a vessel area at the sensing location. As shown in FIG. 5A, the sensing location is in the SVC, thus ultrasound passing "windows" 208 are included in the catheter body so as to permit the ultrasound signal to measure distance to the vessel wall from the center of the catheter. With the same basic arrangement, as shown in FIG. 5B, control wire 206 may be further extended beyond distal tip 190 so as to position ultrasound element 204 within the IVC for sensing at that location. Anchor elements as described below may be optionally employed on the catheter or with ultrasound element 204 in order to help ensure proper positioning of the sensor.

Another embodiment employing an ultrasound sensor is shown in FIG. 5C. In this example, ultrasound element 204 may comprise a sealed housing 820 for containing control, power and other alternative functional modules and provides a self-contained, sealed device. Alternatively one or more of these functions may be provided externally with communication through guide sheath 207 and control wire 206. Guide sheath 207 is delivered through lumen 116B of catheter 106B. Housing 820 also provides support for transceiver 804, which in the case of the illustrated device is a single ultrasound transceiver positioned at the inferior end of the device. Transceiver 804 may utilize one or more ultrasound crystals to measure IVC diameter by emitting an ultrasound pulse, and then detecting the reflection of that pulse from the opposing wall of the IVC. Other modes of detection with ultrasound receivers and/or other transceiver types may be alternatively employed by persons of ordinary skill without departing from the teachings of this disclosure. Housing 820 generally will be provided with the lowest possible profile so as to minimize obstruction of the lumen when positioned in the IVC. In addition, anchor element 808 and/or anchor isolation structure 812 optionally may be provided. Details of anchor element 808 are provided below.

Figure 6B:
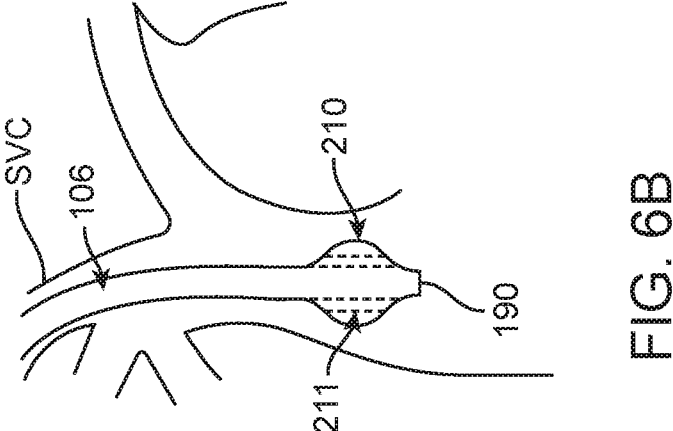
FIGS. 6A and 6B schematically illustrate alternative embodiments using balloon sensors.
Figure 6A:
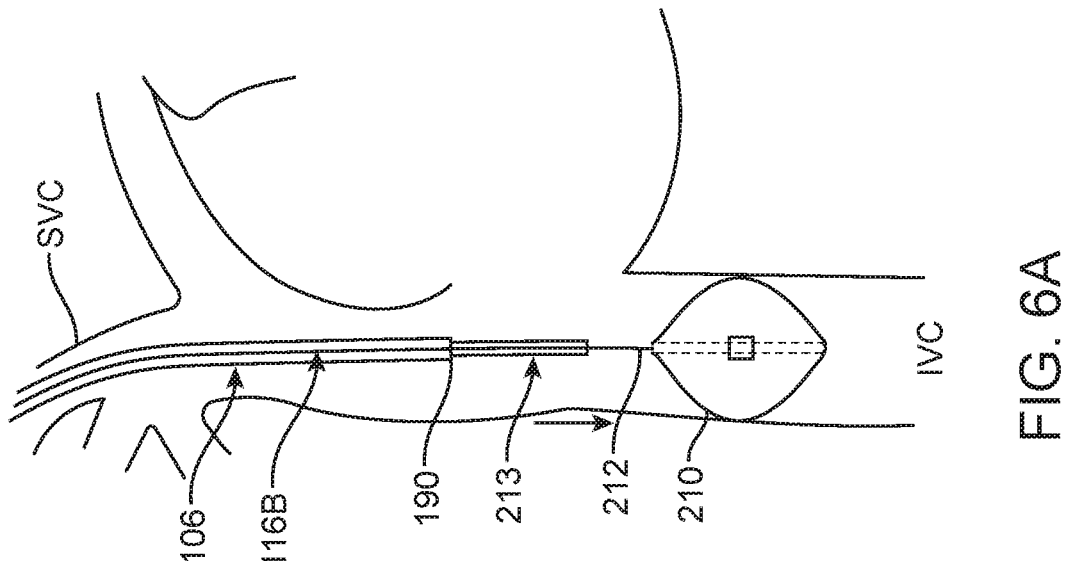

FIGS. 6A and 6B show embodiments utilizing balloons as sensor elements. In FIG. 6B, sensor balloon 210 is formed around catheter 106 just proximal of distal tip 190 so as to provide a measurement at a sensing location in the SVC. In such an embodiment, excentric communication pathway lumen 116A (FIG. 4A) may be used to fill and communicate with balloon 210. Measurements may be accomplished as described above for balloon sensors. To protect balloon 210 during catheter insertion, a sheath such as deployment sheath 118 (FIG. 1) may be used. Once the catheter is properly positioned, sheath 118 is withdrawn to expose balloon 210 for inflation via lumen 116A. Balloon 210 is also provided with blood flow lumens 211 to avoid occlusion of the vessel.

In FIG. 6A, sensor balloon 210 is deployed at the end of low profile balloon catheter 212, which is itself deployed through a sensor communication pathway lumen such as central lumen 116B in FIG. 4B. This embodiment permits measurements via balloon sensor 210 further distally in the IVC. Deployment of balloon catheter 212 may be similar in principle to deployment of an angioplasty balloon. Guiding catheter 213 is advanced through lumen 116B to a position just proximal to the desired sensing location of balloon sensor 210. Balloon catheter 212 is then advanced through guiding catheter 213 to the sensing location, the guiding catheter retracted and balloon sensor 210 is deployed via an inflation lumen in balloon catheter 212. When it is time to withdraw the balloon catheter, the guiding catheter may be reinserted to help ensure complete collapse of and to capture balloon sensor 210. Alternatively, guiding catheter 213 may be omitted and lumen 116B of catheter 106 used as a guiding catheter by first advancing catheter 106 to the sensing location and then withdrawing it to place distal tip 190 in the right atrium.

FIGS. 7A and 7B illustrate further alternative embodiments employing strain gauge-based sensor elements. In the embodiment of FIG. 7A, strain gauge sensor 220 is provided with a plurality of arms 222 that resiliently extend from the outside of catheter 106. Resilient arms 222 may be deployed by withdrawal of deployment sheath 118 (FIG. 1). Strain gauges 224 positioned at the base of each resilient arm detect the amount of strain induced in the arm by its extension to the vessel wall. Strain readings are transmitted to sensor control sub-module 172 (FIG. 1) via sensor communication pathways such as wires 116C, 116D (FIGS. 4C or 4D) and data link 136.

In the embodiment of FIG. 7B, strain gauge sensor 220 is deployed at a sensing location in the IVC at the end of sensor wire 228 in much the same manner as balloon sensor 210 on balloon catheter 212 as shown above in FIG. 6A. A guiding catheter (not shown in FIG. 7B) may be deployed through, for example, central sensor communication lumen 116B also as with the balloon sensor embodiment in FIG. 6A. With the guiding catheter positioned just proximal of the intended sensing location in the IVC, sensor wire 228 with strain gauge sensor 220 is delivered through the guiding catheter to the sensing location. Sensing may be accomplished using strain gauges as described above, communicating through sensor wire 228 and data link 136. Deployment steps are essentially reversed for sensor withdrawal as with the balloon sensor embodiment. Also as above, the separate guiding catheter may be omitted and catheter 106/lumen 116B used for guiding.

In FIG. 7C, deployment of catheter 106E is schematically depicted with Swan-Ganz catheter 230 to facilitate the measurement of pulmonary artery pressure, wedge pressure and right atrial pressure at the same time as monitoring the vena cava (inferior or superior) to manage the dialysis process. Swan-Ganz catheter may be a conventional Swan-Ganz catheter itself defining multiple lumens providing distal balloon 232 communicating with balloon port connector 233, thermistor probe 234 communicating with thermistor connector 235, distal port 236 communicating with distal port connector 237 and proximal port 238 communicating with proximal port connector 239. A complete, conventional Swan-Ganz catheter, such as catheter 230 may be delivered through communication pathway lumen 116E (see FIG. 4E). Alternatively one or more functions of the conventional Swan-Ganz catheter may be incorporated/integrated into catheter 106E itself. For example, rather than provide a separate distal port 238 in catheter 230, the distal port function may be directly performed by communication pathway lumen 116E or other lumen integrated to a wall of catheter 106E. Other Swan-Ganz catheter functions may be similarly directly incorporated into catheter 106E without the need to provide a separate, conventional Swan-Ganz catheter.

As illustrated in FIG. 7C, blood ports 110,112 at distal tip 190 of catheter 106E are positioned in the right atrium to remove and return the patient's blood during a dialysis procedure as discussed above. Control wire 206 extends distally from communication pathway lumen 116A (FIG. 4E) to position rotating ultrasound sensor 204 in the IVC. Rotational ultrasound sensor 204 communicates with control system 104 (FIG. 1) via control wire 206 and data link 136. Alternatively, any other sensors 117 may be employed as elsewhere described herein. In a further alternative, SVC sensing may be optionally or additionally employed, for example as shown in FIG. 3C.

Figure 8:
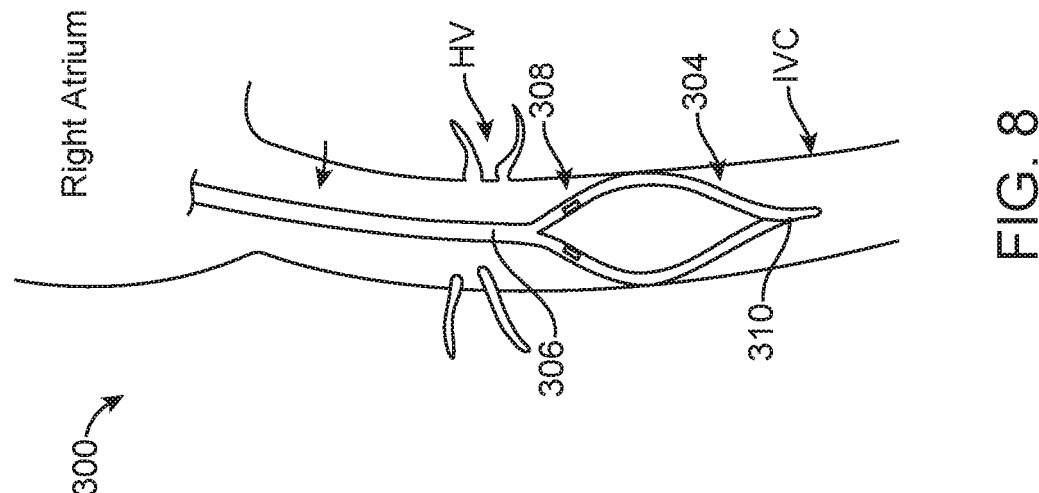
Figure 11:
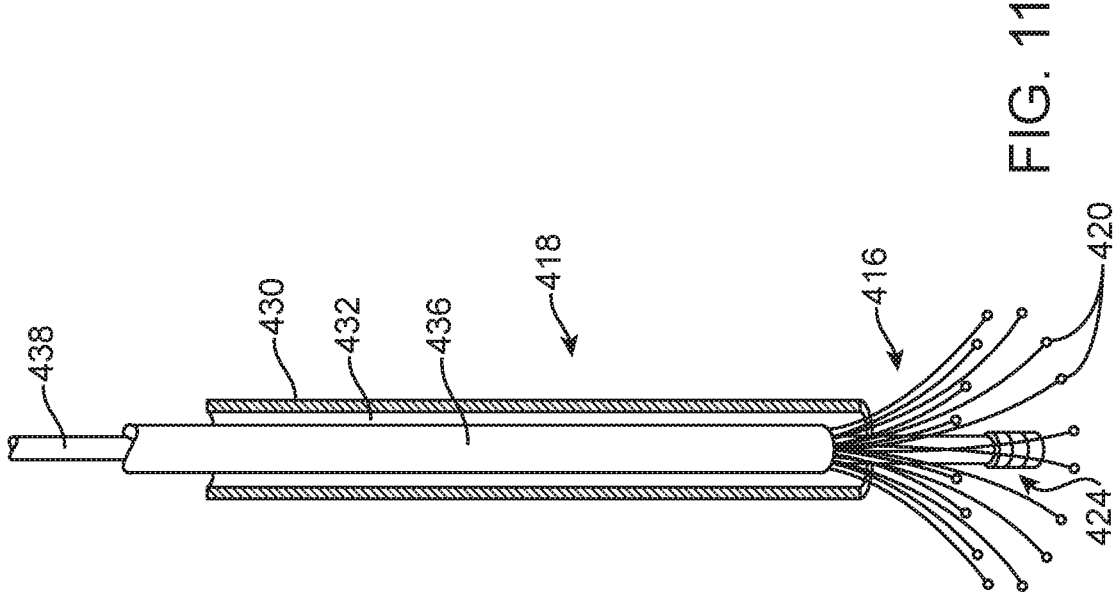

FIGS. 8-11 show various further alternative embodiments of sensor elements configured for employment distally in the IVC. In each embodiment, components shown may be delivered through a communication pathway lumen (such as lumen 116B) of catheter 106B. Catheter 106 would be positioned proximally with respect to the components shown in FIGS. 8-11 and therefore is not shown. In FIG. 8, strain gauge sensor 300 may be provided with two or more arms 304 at the distal end of sensor catheter 306. Arms 304 may be biased radially outwards to lay gently against the IVC walls. This bias may be continuous, or the arms may be held in a collapsed position until a reading is to be taken and then deployed to engage the IVC walls to take the reading. In a further alternative, arms 304 may be deployed using a guide catheter as discussed above. The bias of arms 304 may be relatively gentle, since the pressure in the IVC is typically 5-20 mm HG and any strong bias could tent the IVC open. The separation of arms 304 could be measured in various ways, such as by using one or more strain gauges 308 on one or more arms that electronically sense flexure and transmit readings to a processor outside the body (not shown). Use of a sensor catheter 306 with a central lumen (instead of a control wire) permits additional sensing functionality to be optionally included, such as distal pressure sensor 310.

Figure 9:
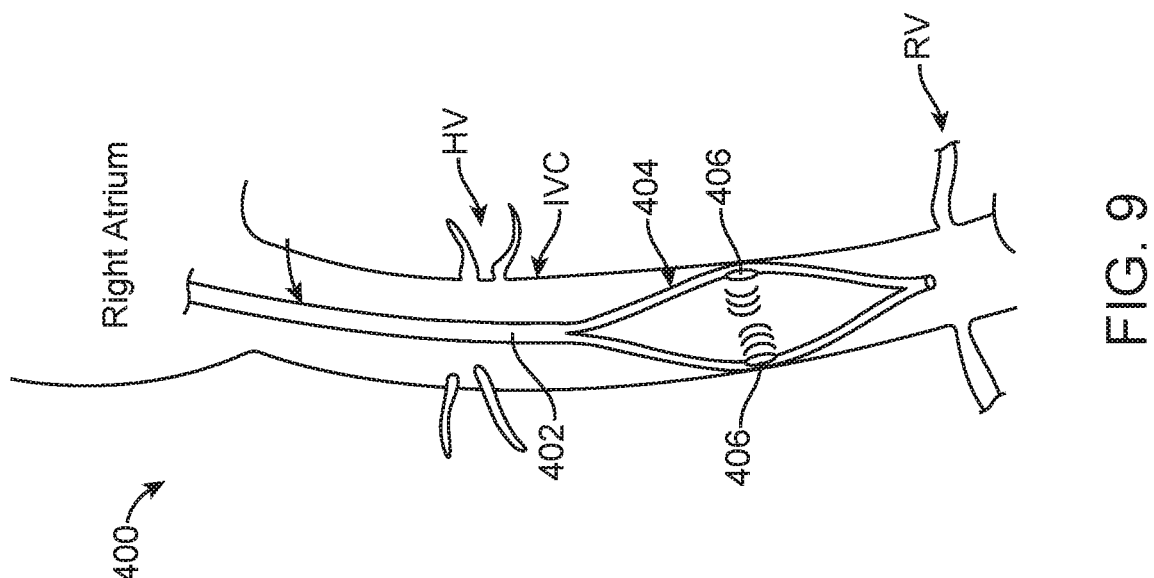
FIGS. 8, 9, 10, and 11 schematically illustrate further alternative sensor embodiments and configurations.

In a further alternative, ultrasound emitters and detectors may also be mounted to each arm to sense the distance between the arms. FIG. 9 shows sensor 400, wherein sensor catheter 402 is provided with two outwardly biased arms 404 with ultrasound transducers 406 on each arm. In some embodiments, more or fewer than two arms and more or fewer than one transducer per arm may be used. A signal generated by transducer 406 can be sensed by another transducer, and a time-of-travel calculation would determine the distance between the arms. A signal may be generated by each transducer 406 in sequence and sensed by each of the others, thereby generating a map of the relative position of each arm.

Figure 10:
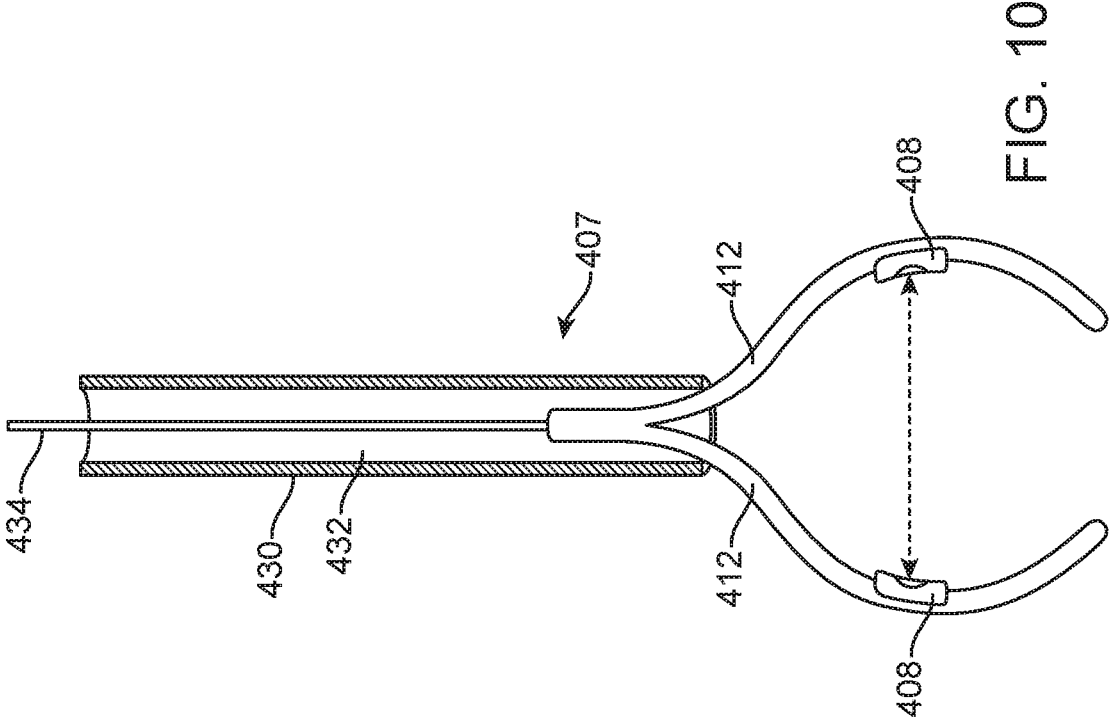

Alternatively, as shown in FIG. 10, sensor 407 with two or more electronic emitter/detectors 408, or two or more separate emitters and detectors, may sense the electrical impedance or capacitance, at one or more frequencies, by inducing or otherwise generating and monitoring an electrical current in order to determine the volume of blood between emitter/detectors 408 or separate emitters and detectors. It should be noted that various arm configurations are possible in each of these embodiments. A pair of arms 412 may have a wishbone shape as shown in FIG. 10, rather than being joined at their ends as with arms 304 of FIG. 8. In a further alternative, a lumen of the catheter may be used to apply suction to ports on the arms to facilitate engagement with the IVC wall. FIG. 10 also illustrates other features of the present disclosure, which may be utilized in combination with other embodiments disclosed herein as well. For example, sheath 430 defines lumen 432, which serves as a guide catheter for control wire 434 and arms 412. Lumen 432 also may be used for additional functionality, such as a delivery or sampling lumen directly in the IVC. Sheath 430 is configured and sized to be delivered through a sensing communication lumen of catheter 106, such as lumen 116A or 116B.

Catheters in embodiments of systems disclosed herein may also include more than two arms, e.g., two pairs of arms arranged orthogonally to each other so as to measure the vessel in two dimensions. In still further embodiments, disclosed catheters may include a larger plurality of arms, e.g., six or more, distributed around the circumference of the catheter and configured to extend radially like spokes of a wheel when deployed. The arms may also comprise, as in sensor 418 shown in FIG. 11, a circumferential array of very thin wires or fibers 416 to create a brush-like structure so as to minimize deformation of the vessel. In one embodiment, each wire/fiber 416 in such an array may comprise an optical fiber through which light may be emitted by emitters 420 and detected by an optical detector 424 on the catheter. Distance may be determined, for example, in accordance with the magnitude of light intensity received by detector 424. Alternatively, an ultrasonic reflector may be placed at the tip of each wire 416 in such an array in place of emitters 420, with an ultrasound transducer located on the catheter centrally within the array in place of detector 424 to emit and detect an ultrasound signal reflected from the reflector on the tip of each wire. In a further alternative, each wire 416 may have an ultrasound detector, measuring the time of travel of an ultrasound signal from one or more ultrasound emitters. Such an embodiment may be configured to provide a two-dimensional profile of the size and shape of the vessel around its entire circumference. Other than arm array as explained above, the structure of sensor 418 is substantially the same as sensor 407 except that it includes at least three concentric members, outer sheath 430, inner delivery catheter member 436, which itself defines a lumen for delivering detector carrying control wire 438. Again, the entire structure is configured and sized to be deliverable through a sensing communication pathway lumen, such as lumen 116B, of catheter 106.

Anchor Configurations

In some clinical situations catheter column stiffness as explained above may be sufficient to maintain the distal tip ports and sensing element in the appropriate locations. However, it may also be desirable to ensure that the sensing element remains fixed at the sensing location by including an expandable and retractable anchor so as to provide a more consistent evaluation of vessel diameter/area and therefore fluid volume. A variety of different anchor designs are possible. Basic features for anchors include retractable/collapsible to minimize profile for entry and removal; engage the wall of the vessel at some point distal to the entry site; and provide sufficient contact with the vessel wall to maintain the location of the measurement element constant. Also, in certain embodiments, catheter column strength between the anchor location and the sensing location should be sufficiently stiff to ensure that the relative distance between them is maintained constant. Alternatively, an isolation structure may be included between the anchor and sensing element so that the anchor does not unduly distort the movement or shape of the vessel at the sensing location.

Figure 12:
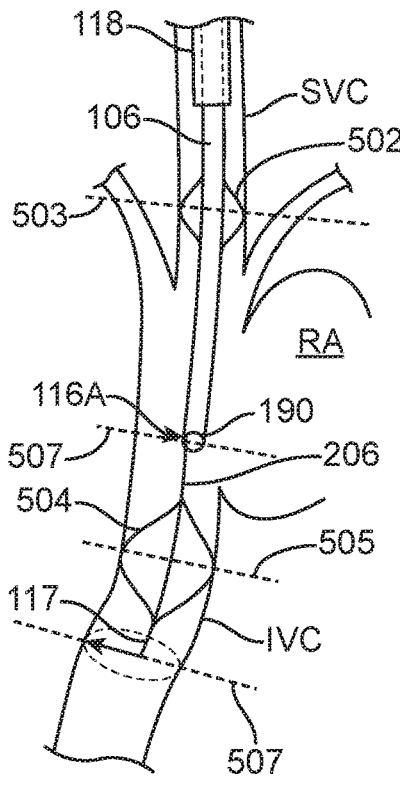
FIG. 12 schematically illustrates anchor locations and aspects of anchor embodiments relative to a patient's vasculature.

FIG. 12 schematically illustrates possible anchor arrangements. As shown therein catheter 106 includes two anchors, proximal shaft anchor 502 and distal anchor 504. Proximal shaft anchor 502 provides a proximal anchor location 503 in the SVC or higher and above the blood ports in distal tip 190. Distal anchor 504 provides a distal anchor location 505 below the right atrium and catheter blood ports. As illustrated anchor 504 is positioned with anchor location 505 above or proximal to sensor element 117 at sensing location 507. An inverse configuration is also possible with anchor location 505 below sensing location 507. Also, it is not required that there be two anchors as illustrated. Either is optional and either may be included or omitted in specific designs based on clinical needs and catheter configuration considerations.

Either or both of proximal shaft anchor 502 and distal anchor 504 may be formed as any suitable type of expandable/collapsible and retractable anchor, for example the anchor embodiments described below. Proximal shaft anchor 502 is formed on the body of catheter 106 and may be deployed, for example, by retracting deployment sheath 118. Distal anchor 504 is deployed on control wire 206, or alternatively may be deployed from a separate guide sheath, either of which are deliverable through a sensing communication pathway lumen, such as excentric lumen 116A (FIG. 4A). Where a control wire is used, optionally a guide sheath may be used or catheter 106 and the communication pathway lumen may functionally serve as the guide sheath with catheter 106 first advanced to anchor location 505, the anchor deployed and then the catheter may be withdrawn to the dialysis position proximate the right atrium. Steps may be reversed for retraction of the anchor.

Figure 13A:
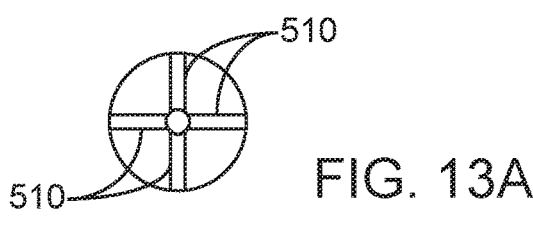
FIGS. 13A and 13B schematically illustrate embodiments of resilient arm anchors.
Figure 13B:
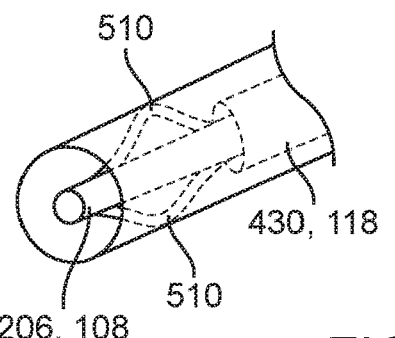

FIGS. 13A and 13B illustrate one alternative embodiment of an anchor employing collapsible arms 510, which may be made from a biased wire or shape memory material such as nitinol. Two, three or four arms 510 may be provided. Arms 510 may be formed on a control wire or the body of catheter 106 as discussed above. Deployment may be accomplished by use of a deployment sheath, such as deployment sheath 118 or sheath 430 (FIG. 10),whereby arms 510 self-deploy due to shape and resiliency when released or they may be deployed by a relative sliding motion between to control wires.

Figure 14A:
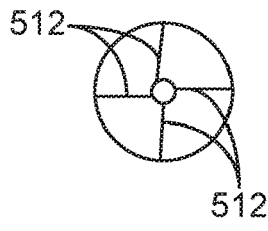
FIGS. 14A and 14B schematically illustrate embodiments of resilient finger anchors.
Figure 14B:
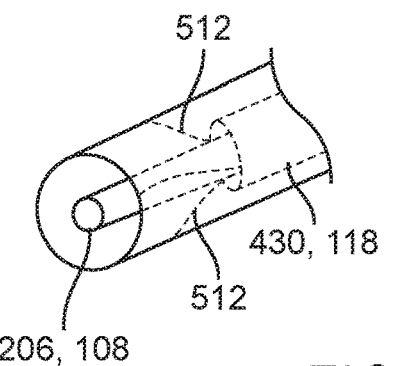
Figure 15:
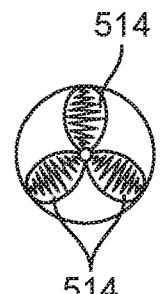
FIG. 15 schematically illustrates an embodiment of a balloon anchor.

FIG. 14A and 14B illustrate another alternative anchor embodiment employing collapsible resilient fingers 512. Once again, two, three or four fingers may be provided. Fingers 512 maybe be, for example, formed of nitinol wire on the body of catheter 106 or on control wire 206 and released via a deployment sheath such as sheath 118 or sheath 430. FIG. 15 illustrates an end view of yet another alternative anchor embodiment comprising one or more anchor balloons 514. Inflation passages for balloon anchors 514 may be provided through communication pathway lumens 116 as previously described with respect to balloon sensor embodiments. Provisions also must be made for blood flow so as to not occlude the vessel at the anchor location. In the illustrated embodiment, three balloon anchor leaves are provided with passages therebetween for blood flow. Blood flow lumens also may be provided through the balloon.

Returning to FIG. 5C, a further anchor embodiment is shown therein. In this embedment, anchor element 808 is connected at the superior end of sensor housing 820. Anchor element 808 as depicted in this embodiment includes a single anchor wire 828 configured in a generally figure-eight or double helix shape. Alternatively, the same or similar configurations can be provided with two or more wires. Anchor wire 828 is pinned to a telescoping deployment mechanism at both its inferior end and superior end. In this case, control wire 206 is formed as a telescoping deployment mechanism including inner and outer sliding members. Relative motion between the inner and outer members moves anchor wire 828 from a collapsed position to a deployed or anchoring position. The inner member of deployment member is secured to housing 820, through anchor isolation structure 812.

As mentioned above, in some embodiments it may be desirable to provide an anchor isolation structure between the anchor and sensing element. In such embodiments, the spacing between the sensor element, such as transceiver 804, relative to the anchor, such as anchor element 808, is provided by an anchor isolation structure, such as structure 812. In general, it may be preferred that the anchor element be positioned sufficiently distant from the sensor element so as to not have an effect upon the vessel size or shape at or close to the sensing location due to the anchoring force imparted to the vessel wall. This consideration is especially important with respect to anchors configured to be deployed in the IVC as the IVC has a relatively compliant wall structure compared to other vessels. As shown, for example in FIG. 5C, anchor isolation structure 812 ensures a desired positioning of the sensor element with respect to the anchor location, which may be approximately ½ to 4 times the IVC diameter as indicated above, typically in the range of about 2-6 cm, and in some cases more preferably about 3-5 cm. In general, the IVC has a somewhat oval cross section with a minor axis of the oval extending in the anterior-posterior direction and a major axis extending in the lateral-medial direction. It is thus desirable to minimize any effect of the anchor on this natural oval shape at or close to the sensing location.

FIG. 16 shows the distal end of a further embodiment employing both a proximal sensing element and proximal shaft anchors. In this embodiment, sensing arms 902 are mounted on body 108 and a pair of resilient anchor wires 904 are secured to catheter 106 further proximally, generally positioned to engage the vessel wall in the SVC. Once distal end 190, with blood ports 110, 112, is positioned as desired, deployment sheath 118 may be withdrawn using hub 122 (FIG. 1). Withdrawal of deployment sheath 118 first deploys sensing arms 902 and then releases resilient anchor wires 904 to engage the vessel wall. Sensing arms 902 include strain gauges 906 to detect the angle of deployment and changes therein and send signals indicative thereof to sensor control sub-module 172 via communication pathway wires, e.g. wires 116C or 116D, and data link 136. (See FIGS. 1, 4C and 4D).

Patient-Specific Treatment Optimization

Initially, it is to be noted that while embodiments of the present disclosure are exemplified by reference to hemodialysis, the teachings and embodiments of the present disclosure are also applicable in other patient fluid volume modifying treatments or procedures. During a fluid volume modifying treatment, such as a hemodialysis session, sensor 117 (which may be any of the sensor types disclosed above) located on the catheter 106 (which may be any of the catheter configurations disclosed above) provides a series of vessel dimension or area measurements. The sensor measurements are interpreted within a context of collapsible vessel during fluid loading where, generally speaking, area collapsibility is maximized at relative euvolemia, increasing area and decreasing area collapsibility are associated with increasing volume towards hypervolemia and decreasing area and decreasing collapse are associated with movement from euvolemia towards hypovolemia. This relationship defines an area-collapsibility curve that is essentially an "n" shaped curve as shown in FIG. 17. More details on collapsibility and relationship to patient euvolemia and hypervolemia are discussed in Applicant's patent application publication WO 2018/031714 (corresponding to U.S. patent application Ser. No. 16/271,798, filed Feb. 9, 2019, entitled "Systems and Methods for Patient Fluid Management", which is incorporated by reference herein).

As the dialysis procedure (or other patient fluid volume modifying procedure) progresses, excess fluid is removed from the patient's blood via dialysis and the patient's fluid status will move from right to left along the "n" shaped curve of FIG. 17. It should be noted that this may result in increasing or decreasing collapse, depending on the patient's starting fluid volume status. This information on the fluid volume status of the patient can then be used as a key input into the dialysis process for a number of different aims, including, in particular, optimizing (typically shortening) the dialysis procedure for specific patients and patient conditions by running the process as fast as tolerable until the vessel dimensions indicate that the patient is tending towards hypovolemia. At this point the process could be stopped or the dialysis rate could be reduced during a stabilization phase, thus allowing the extravascular fluid to refill into the vascular space and then be extracted from the patient, allowing a drier "dry weight" to be achieved. Dialysis parameters that may be modulated based on the monitored vascular dimension include, but are not necessarily limited to, blood pressure at various points in the extracorporeal circuit, blood flow rate through the extracorporeal circuit, dialysate pressure, temperature, O2 saturation, motor speed, dialyzer membrane pressure gradient. Optimized treatment as described herein may result in a longer duration between dialysis sessions, a healthier patient between sessions and/or a reduced mortality prior to dialysis on Mondays (where clinical data has shown most deaths occur during the longest duration between sessions, which is most commonly over the weekend).

Advantages of optimized treatment according to the present disclosure may be illustrated by contrast with standard dialysis techniques as illustrated in FIG. 18. Curve "A" in FIG. 18 (from Katzarski et al. "A Critical Evaluation of Ultrasound Measurement of Inferior Vena Cava Diameter in Assessing Dry Weight in Normotensive and Hypertensive Hemodialysis Patients," AJKD, vol. 30, no. 4, October 1997, pp. 459-65) represents change in IVC dimension over time during and after a conventional dialysis procedure, wherein Point "C" indicates the point of cessation of dialysis based on a target patient fluid state. Curve "B" in FIG. 18 represents change in IVC dimension over time during an improved dialysis procedure based on the teachings herein described. As is clinically understood, removal of fluid during dialysis results in a reduction in IVC diameter as fluid is removed. During standard dialysis, vessel diameter reduces over time to a point (C) where a targeted fluid state is indicated and dialysis is stopped. However, as represented by Curve "A" to the right of Point "C", once the dialysis process is stopped in traditional treatment, the IVC tends to refill due to the refilling of the intravascular space, including the IVC, from the extravascular space. This is not ideal for the dialysis patient as they are not as "dry" as they appear at the end of the session and are therefore not optimally treated.

Volume overload is accepted as being a predictor of poor outcomes for dialysis patients and this is demonstrated by the fact that the highest mortality of dialysis patients occurs on the day before their dialysis session. It is therefore suggested that removing more of this extravascular fluid would improve the outcomes of these patients and monitoring the IVC provides a unique insight to facilitate this. By utilizing continuous IVC monitoring as can be provided by embodiments of system 100 described herein, a specific patient's dialysis treatment may be run aggressively for an initial, first stage or period, as indicated by the relatively steep slope of Curve "B" to the left of Point "C". More aggressive initial treatment would involve faster flow rates and higher filtration. This would mainly act to remove blood from the intravascular space more quickly and progress toward a target point (C) and could be monitored and detected by decreasing IVC area and increasing IVC collapse as determined via sensors 117 on catheter embodiments of catheter 106. The rate of fluid removal in the first stage may be determined by a health care provider for each patient based on patient-specific parameters such as URR (urea reduction ratio), Kt/V (blood flow rate by time over fluid volume), current or historical fluid volume information, heart rate, respiration rate, height, weight, age, time since last dialysis, and general health state. While the rate of fluid removal will in each case typically be determined for specific patients, a general guideline may be defined as continuing the first stage/higher removal rate until the monitored vascular dimension (for example IVC area) is reduced by about 30%-50% and the vessel collapse passes its maximum and begins to stabilize or reduce. Stabilization of vessel collapse as a transition point from first stage to second stage treatment is reflected in the dialysis session time plots of FIGS. 19 and 20.

In the improved process, second stabilization stage may be implemented after the initial target point is reached, as shown by Curve "B" to the right of Point "C". This second, stabilization stage, may be individually optimized for specific patients to hold the intravascular volume down by modifying the dialysis process parameters under monitoring by system 100, and thus provide the in vivo conditions for the extraction of fluid from the extravascular space, to the intravascular space and out of the body via the dialysis process. This removal of the extravascular fluid then results in the patient achieving a 'drier' state, with more volume removed, primarily from the extravascular space, in the same dialysis time, or potentially in a shorter time, while reducing or eliminating the risk of hypovolemia. As shown in FIGS. 19 and 20, during the second stage stabilization, fluid removal can be carefully modulated with dialysis parameters by monitoring of the IVC dimension such that vessel area and vessel collapse may be held relatively constant with intravascular fluid extracted at a relatively constant rate so as to slowly bring down extravascular fluid volume.

FIGS. 3A and 3B illustrate embodiments of possible therapy titration schedules over the patient fluid state ranges based on the teachings of the present disclosure. Because IVC diameter/area changes more accurately reflect changes in patient fluid volume consistent with actual fluid state, IVC diameter or area measurements can be used to help titrate treatments more precisely and adjust the therapeutic intervention more subtly and incrementally, rather than just using a hard threshold as is now the clinical norm. Use of IVC diameter or area measurements also allows the flexibility of potentially titrating patients to a personalised volume, for example, keeping a patient with reduced cardiac ejection fraction (HFrEF) at a wetter point, while maintaining a patient with preserved cardiac ejection fraction (HFpEF) at a drier point.

FIG. 3A describes one possible treatment algorithm in this regard in which patient therapy is reduced when the patient's flood volume comfortably falls in the mid-range of the euvolemic region. In this treatment algorithm example, in which curve (T) represents a relative therapy level plotted against patient fluid volume, therapy is increased relatively rapidly once the patient's fluid volume moves from the mid-range of the euvolemic region as indicated by monitored changes in the IVC diameter or area. Such a treatment algorithm may be appropriate, for example, for a patient that is known to have a slow response to therapy in order to avoid having the patient move too far into the hypovolemic or hypervolemic regions before responding to the treatment. FIG. 3B describes another possible treatment algorithm based on the teachings of the present disclosure. In this example, relative therapy curve (T) is flatter across the majority of the euvolemic region (D) and only significantly increases once fluid volume, as determined based on sensed changes in IVC diameter or area, moves into one of the predefined early warning regions $O_E$ or $R_E$ that have been determined to be clinically appropriate for the specific patient being monitored. For illustration purposes, curve $A_2$ from FIG. 1 (representing change in IVC diameter/area vs. fluid volume) is superimposed over treatment curve (T) in FIG. 3B so that the relative relationship between IVC diameter/area change and treatment algorithm in this example may be better appreciated.

FIG. 3C schematically illustrates practical application of the relationships illustrated in FIG. 1 and potential advantages of treatment algorithms such as described in FIGS. 3A and 3B, based on sensed changes in IVC diameter or area as disclosed herein. In FIG. 3C, relative patient fluid volumes for hypothetical patients (whose therapy is titrated according to a treatment algorithm as described above) are plotted against relative time. Curves FVR1 and FVR2 thus represent two hypothetical examples of patient fluid volume response to therapy over time. In each case, applying a treatment algorithm such as described in the examples of FIGS. 3A or 3B, patient therapy can be titrated more accurately with respect to actual fluid state within the euvolemic region such that therapy may be applied at appropriate times earlier and more gradually to ensure that overall patient fluid volume stays within or as close as possible to the euvolemic region.

IVC diameter or area measurements also may be used in combination with other diagnostic signals to provide guidance on therapeutic intervention, e.g. diuretics versus vasodilators. When used with intervention, the IVC diameter or area measurement time dynamics response may be used to give information on the fluid status/distribution of the patient to guide therapy intervention. Response of IVC diameter or area measurements to a perturbation, e.g., physical activity, can cause sympathetic nerve response and fluid redistribution. Looking at changes in IVC diameter or area will thus provide information on fluid volume status. In other words, an act as simple as a leg raise may cause a fluid change/redistribution that could also provide information on fluid volume status that would not be visible with pressure-based systems. Thus, in certain embodiments, at-risk patients may have continuous or near-continuous monitoring of IVC diameter or area changes during physical activity.

Sensed changes in IVC diameter or area also may be combined with other parameters such as with BNP or pressure/edema signals to help guide therapy intervention or differentiate patient phenotype (HFrEF v HFpEF). Examples include detection of low collapsibility plus peripheral edema as an indication for diuretic therapy or detection of low collapsibility without peripheral edema as an indication for indicate vasodilator therapy. Combination of monitoring IVC diameter or area changes with implanted pressure-based monitors (in the IVC, right atrium, right ventricle, pulmonary artery, left atrium, or other vessel) also may permit determination of abdominal pressure and flow in the IVC. In addition, the IVC monitoring device of the invention may include additional sensors to measure non-dimensional parameters within the IVC such as blood flow rate and venous pressure. Further, measurement of the dimensions or non-dimensional parameters of other vessels, such as the superior vena cava, pulmonary artery, or heart chambers, may in some cases be advantageous to supplement IVC measurement. In such cases, dimensional measurement devices similar to the IVC monitoring device of the present invention may be configured for implantation in such other vessels. In such embodiments, the methods and systems of the invention may be adapted to receive such supplementary data from these sources and incorporate such data in the determination of fluid status, heart failure status, appropriate thresholds for communicating alerts or messages, or therapeutic treatment plans or recommendations.

Use of IVC diameter or area measurements also leads to the development of new systems such as closed-loop systems for therapy intervention as described herein. Examples include modification of a standard dialysis system filtration rate from a constant rate to a faster or variable rate using information that was previously unavailable to the clinician or patient. In one example, as illustrated in FIG. 4A, IVC diameter or area measurements may provide faster dialysis treatment in a closed-loop system, such as described below, by guiding higher filtration rates while the fluid load is high and inform reducing filtration rate as the fluid is reduced, ultimately resulting in a faster and safer treatment. Hypotensive events may occur in patients undergoing dialysis due to fluid removal occurring too rapidly. FIG. 4A plots patient fluid volume against rate of dialysis for a closed-loop system based on embodiments described herein, which may allow for more efficient dialysis, e.g., fast enough to remove fluid without the side effects of fast fluid removal. When ultrafiltration (UF) is constant, the degree of vascular refilling will differ from patient to patient, therefore using additional information provided by IVC diameter or area measurements may allow the UF rate to be more accurately individualized in a time dependent fashion over the course of the dialysis session for specific patients. IVC diameter or area measurement information may be combined with other diagnostic tools such as blood pressure monitoring to more accurately estimate fluid volume status as a basis for altering the rate of filtration.

FIG. 4B illustrates another embodiment in which alteration of dialysis filtration rate may be based on periodic assessments of IVC diameter or area change, e.g., a percent change in IVC volume metric per hour coinciding with a total desired volume that needs to be removed. (Each downward arrow in FIG. 4B indicates relative time of each assessment.) This is another alternative approach to control of UF rate, which allows increased accuracy and individualization of treatment for specific patients in a time dependent fashion over the course of a dialysis session. Another alternative dialysis control methodology is described in FIG. 4C in which the IVC volume metric rate of change, based on measured changes in IVC diameter or area, is plotted against time through a hypothetical dialysis session. Employing systems as described herein, time-based check points may be provided, at which time the measured IVC volume metric is checked against predefined patient specific targets. At each check point, UF rate may be altered as needed to direct the patient more efficiently and smoothly to the final fluid volume target. Compared to existing systems, which rely primarily on dry weight estimation based on inter-dialytic weight gain, employing methodologies as described in any of FIGS. 4A, 4B and 4C with systems disclosed herein provides for increased individualization of UF rate for specific patients over the course of the dialysis session.

In another example, illustrated in FIG. 5A, an implanted drug pump or device may be provided, for example as a closed-loop dialysis management system. In such a system, at a hypervolemic end of the scale the device runs at high speed/delivers large load. As volume is reduced the device slows. This allows time for the interstitial fluid to return to the intravascular space. As the fluid load approaches hypovolemia the device speed/drug load rate could increase proportionally to avoid a hypovolemic state. Such control requires knowledge of incremental changes in fluid state across the euvolemic ranges, which is provided by methodologies and systems described herein. As a point of reference, curve A2 indicating relative IVC diameter or area measurement (from FIG. 1) is superimposed on the treatment curve (T) in FIG. 5A. In yet a further example, illustrated in FIG. 5B, a closed loop system according to embodiments described herein allows for volume control-based therapy delivery modulated based on measured changes in IVC diameter or area. In this example, at either end of the euvolemic region (D), therapy delivery, e.g., drug delivery such as a diuretic or dialysis filtration, may be altered up ($T_u$) or alerted down ($T_d$) in accordance with IVC diameter or area measurements.

As mentioned above, IVC collapsibility or IVC CI are parameters that may be generated to facilitate diagnostic decisions based on IVC metrics. FIG. 7 illustrates one exemplary algorithm for determination of IVC collapsibility on which a treatment algorithm may be based. One example of such a treatment algorithm is illustrated in FIG. 8. Another example is described below in Table I. Plots A and B in FIG. 7 show two different IVC collapsibility conditions plotted as diameter versus time over several respiratory cycles (in this case based on ultrasound detection, but diameter/area detection of the IVC may be based on any other modalities described herein to achieve similar results).

Based on a calculated IVC collapsibility, a treatment algorithm such as shown in FIG. 8 may be employed. Based on several published research studies, an IVC Collapsibility Index (IVC CI) of 15% or less indicates significant fluid overload, which may imply an imminent risk of acute decompensation. An IVC CI of 20-30% might be considered normal, and an IVC CI of greater than 40% might indicate a hypovolemic state. These percentages may be adjusted for patients with certain conditions. For example, a patient with heart failure with reduced ejection fraction might preferably be maintained at a lower IVC CI (i.e., with more circulating blood volume) to maximize cardiac output.

In developing any treatment algorithm a starting point is existing clinical guidelines, which a physician may then customize to an individual patient. Consistent with medically accepted best practices changes to treatment algorithms are made in conjunction with normal clinical exam and other data that treating physician has available. Embodiments described herein offer a new and powerful tool in this regard by making available regular IVC diameter or volume measurements without requiring a patient to be in a clinical setting and, potentially, providing continuous information on IVC volume metrics in near-real time.

With more and more accurate data on IVC volume metrics available to the healthcare provider based on systems described herein, more refined treatment algorithms may be devised. Such algorithms also may include a significant home-care component that was not previously possible. Table II below sets forth an alternative treatment algorithm in the form of IVC metrics to guide to patient volume status over the course of 4-5 respiratory cycles (IVC metrics employed in this algorithm include maximum and minimum diameters & IVCCI calculation (max−min)/max)×100).

TABLE II

| | Example of Treatment Algorithm | | | |
|---|---|---|---|---|
| Measurement | IVC Ø < 14 mm and IVCCI > 75% | IVC Ø < 21 mm and IVCCI > 50% | IVC Ø < 21 mm and IVCCI < 50%, IVC Ø > 21 mm and IVCCI > 50% | IVC Ø > 21 mm and IVCCI < 50% , sniff or < 20% quiet inspiration |
| Characterize | Low IVC Ø and high IVCCI (hypovolemic) | Normal IVC Ø and IVCCI (euvolemic) | Intermediate IVC Ø and IVCCI (intermediate) | Dilated IVC Ø, low IVCCI (hypervolemic) |
| Trend | Trending below normal | Trending within normal | Trending towards thresholds | Trending above normal |
| Assessment | Review diuretic dosing in line with the trend in IVC metric | No medication changes required based on normal metrics | Increase monitoring frequency | Consider increasing or adding diuretic |
| Intervention or no intervention | If on diuretic and other signs of hypovolemia are present omit half a diuretic dose until signal changes e.g. stop diuretic for 24-48 hrs<br>If not on diuretics, consider liberalization of oral fluid/salt<br>If on vasodilators, lower dose or discontinue if postural hypotension present | Continue current treatment regimen in line with current guideline driven standard of care, ensuring optimal dosing of one medicine | Consider up-titration of current medications in line with current guideline standard of care | Add or increase loop diuretic (e.g. 40 mg furosemide or 1 mg bumetanide)<br>Add or increase thiazide or thiazide-like diuretic dose<br>Consider switching from furosemide to IV loop diuretic: initiate with 20-80 mg |
| Follow up | Re-evaluate IVC trends in response to diuretic change for 2-3 days; adjust thresholds if necessary | Evaluate weekly to maintain stability | Evaluate 2x weekly to maintain stability; adjust thresholds if necessary | Re-evaluate IVC trends in response to diuretic change for 2-3 days<br>Measure renal function within 5-10 days of diuretic change: if creatinine increase by 20% or greater, consider reducing or |

TABLE II-continued

Example of Treatment Algorithm

| | | | | discontinuing diuretic or reducing the vasoactive medication |
|---|---|---|---|---|
| Additional actions | n/a | n/a | n/a | If no IVC response or continued trend elevations observed, consider vasodilator change |

Computer—Software Implementation

It is to be noted that any one or more of the aspects and embodiments described herein, such as, for example, related to communications, monitoring, control or signal processing, may be conveniently implemented using one or more machines programmed according to the teachings of the present specification. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any non-transitory medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, smart watch, etc.), a web appliance, a network router, a network switch, a network bridge, any machine capable of executing a sequence of instructions that specify an action to be taken by that machine, and any combinations thereof. In one example, a computing device may include and/or be included in a kiosk.

FIG. 26 shows a diagrammatic representation of one embodiment of a computing device in the exemplary form of an IVC diameter/area measuring implant control and communication system 1000 within which a set of instructions for causing an implant control and communication system, such as a waveform generator, an oscilloscope, an EFM circuit, or an implant, among other systems and devices disclosed herein, to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1000 includes a processor 1004 and a memory 1008 that communicate with each other, and with other components, via a bus 1012. Bus 1012 may include any of several types of bus structures including, but not limited to, a memory bus, a memory controller, a peripheral bus, a local bus, and any combinations thereof, using any of a variety of bus architectures.

Memory 1008 may include various components (e.g., machine-readable media) including, but not limited to, a random access memory component, a read only component, and any combinations thereof. In one example, a basic input/output system 1016 (BIOS), including basic routines that help to transfer information between elements within control and communication system 1000, such as during start-up, may be stored in memory 1008. Memory 1008 may also include (e.g., stored on one or more machine-readable media) instructions (e.g., software) 1020 embodying any one or more of the aspects and/or methodologies of the present disclosure. In another example, memory 1008 may further include any number of program modules including, but not limited to, an operating system, one or more application programs, other program modules, program data, and any combinations thereof.

Control and communication system 1000 may also include a storage device 1024. Examples of a storage device (e.g., storage device 1024) include, but are not limited to, a hard disk drive, a magnetic disk drive, an optical disc drive in combination with an optical medium, a solid-state memory device, and any combinations thereof. Storage device 1024 may be connected to bus 1012 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1024 (or one or more components thereof) may be removably interfaced with control and communication system 1000 (e.g., via an external port connector (not shown)). Particularly, storage device 1024 and an associated machine-readable medium 1028 may provide nonvolatile and/or volatile storage of machine-readable instructions, data structures, program modules, and/or other data for control and communication system 1000. In one example, software 1020 may reside, completely or partially, within machine-readable medium 1028. In another example, software 1020 may reside, completely or partially, within processor 1004.

Control and communication system 1000 may also include an input device 1032. In one example, a user of control and communication system 1000 may enter commands and/or other information into control and communication system 1000 via input device 1032. Examples of an input device 1032 include, but are not limited to, an alphanumeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1032 may be interfaced to bus 1012 via any of a variety of interfaces (not shown) including, but not limited to, a serial interface, a parallel interface, a game port, a USB interface, a FIREWIRE interface, a direct interface to bus 1012, and any combinations thereof. Input device 1032 may include a touch screen interface that may be a part of or separate from display 1036, discussed further below. Input device 1032 may be utilized as a user selection device for selecting one or more graphical representations in a graphical interface as described above.

A user may also input commands and/or other information to control and communication system 1000 via storage device 1024 (e.g., a removable disk drive, a flash drive, etc.) and/or network interface device 1040. A network interface device, such as network interface device 1040, may be utilized for connecting control and communication system 1000 to one or more of a variety of networks, such as network 1044, and one or more remote devices 1048 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1044, may employ a wired and/or a wireless mode of communication. In general, any network topology may be used. Information (e.g., data, software 1020, etc.) may be communicated to and/or from control and communication system 1000 via network interface device 1040.

Control and communication system 1000 may further include a video display adapter 1052 for communicating a displayable image to a display device, such as display device 1036. Examples of a display device include, but are not limited to, a liquid crystal display (LCD), a cathode ray tube (CRT), a plasma display, a light emitting diode (LED) display, and any combinations thereof. Display adapter 1052 and display device 1036 may be utilized in combination with processor 1004 to provide graphical representations of aspects of the present disclosure. In addition to a display device, control and communication system 1000 may include one or more other peripheral output devices including, but not limited to, an audio speaker, a printer, and any combinations thereof. Such peripheral output devices may be connected to bus 1012 via a peripheral interface 1056. Examples of a peripheral interface include, but are not limited to, a serial port, a USB connection, a FIREWIRE connection, a parallel connection, and any combinations thereof.

The foregoing has been a detailed description of illustrative embodiments of the invention. It is noted that in the present specification and claims appended hereto, conjunctive language such as is used in the phrases "at least one of X, Y and Z" and "one or more of X, Y, and Z," unless specifically stated or indicated otherwise, shall be taken to mean that each item in the conjunctive list can be present in any number exclusive of every other item in the list or in any number in combination with any or all other item(s) in the conjunctive list, each of which may also be present in any number. Applying this general rule, the conjunctive phrases in the foregoing examples in which the conjunctive list consists of X, Y, and Z shall each encompass: one or more of X; one or more of Y; one or more of Z; one or more of X and one or more of Y; one or more of Y and one or more of Z; one or more of X and one or more of Z; and one or more of X, one or more of Y and one or more of Z.

Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve aspects of the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A dialysis catheter system, comprising:
an elongate body with a proximal end configured to be manipulated outside a patient's body and a distal end configured to extend into the patient's vasculature, the distal end defining blood removal and return ports communicating with internal blood removal and return lumens extending through the elongate body to the proximal end;
a sensing pathway disposed in or on the elongate body;
a sensor configured to dynamically measure changes in a diameter or area of the vessel, the sensor supported by the elongate body so as to be positioned in the SVC or IVC with the distal end blood removal and return ports positioned at a treatment location in the patient's vasculature, wherein the sensing pathway is configured to provide communication between the sensor and the proximal end of the elongate body;
a dialyzer communicating with the blood removal and return lumens;
at least one pressure gauge and at least one pump to control blood flow through the dialyzer; and at least one processor and memory containing instructions for control of the dialyzer based on signals from the sensor received through the sensing pathway, and wherein the at least one processor communicates with the at least one pressure gauge and at least one pump to control a rate of dialysis treatment delivered by the dialyzer; and one or more anchor means for anchoring at least one of the distal end of the elongate body or the sensor at a desired location in the SVC or IVC, the anchor means comprising a catheter hub at the proximal end of the elongate body configured to be positioned outside the patient's body and fixed relative to the patient's body, and a predetermined length and stiffness of the elongate body configured and dimensioned to position and maintain the distal end at the desired location in the SVC or IVC with the catheter hub.

2. The dialysis catheter system of claim 1, further comprising a retractable deployment sheath disposed around the elongate body.

3. The dialysis catheter system of claim 1, wherein the sensing pathway comprises a third lumen defined within the elongate body.

4. The dialysis catheter system of claim 3, further comprising an elongate control member wherein the sensor is disposed at a distal end of the elongate control member and the elongate control member is deployable through said third lumen.

5. The dialysis catheter system of claim 1, wherein the anchor means further comprises plural individual resilient members extending from an anchor support.

6. The dialysis catheter system of claim 1, wherein an anchor means further comprises at least one inflatable balloon member disposed on an anchor support, said at least one balloon defining passages for blood flow therethrough.

7. The dialysis catheter system of claim 1, wherein the elongate body comprises an anchor support for an anchor means and retraction of a retractable deployment sheath disposed around the elongate body at least in part deploys the anchor means.

8. The dialysis catheter system of claim 1, further comprising an elongate control member, and wherein
the sensing pathway comprises a third lumen defined within the elongate body;
the sensor is disposed at a distal end of the elongate control member and the elongate control member is deployable through said third lumen; and
the elongate control member comprises the anchor support and relative movement between the third lumen and the elongate control member at least in part deploy an anchor means.

9. The dialysis catheter system of claim 8, wherein the sensing pathway comprises at least one wire embedded in or disposed on a wall of the elongate body or a wall of the elongate control member.

10. The dialysis catheter system of claim 1, wherein at least one said sensor comprises one or more of an ultrasound sensor, an expandable and collapsible coil forming a resonant circuit, one or more strain gauges disposed between two extendable arms, an inflatable balloon, an impedance sensor comprising a series of electrodes disposed on a conductive framework configured to contact and expand and collapse with the vessel wall or a light sensor.

11. The dialysis catheter system of claim 1, wherein the elongate body comprises a peripheral outer wall divided by a central inner wall to form parallel blood return and removal lumens therein.

12. A diagnostic and dialysis catheter system, comprising:
a dialysis catheter comprising:
an elongate body with a proximal end configured to be manipulated outside a patient's body and a distal end configured to extend into the patient's vasculature, the distal end defining blood removal and return ports communicating with internal blood removal and return lumens extending through the elongate body to the proximal end,
a sensing pathway disposed in or on the elongate body,
a sensor configured to dynamically measure changes in a diameter or area of the vessel, the sensor supported by the elongate body so as to be positioned in the SVC or IVC with the distal end blood removal and return ports positioned at a treatment location in the patient's vasculature, wherein the sensing pathway is configured to provide communication between the sensor and the proximal end of the elongate body,
a catheter hub disposed at the proximal end of the elongate body, the catheter hub configured to provide connection and communication for the blood removal and return lumens and the sensing pathway with a therapy system, and
a sheath hub disposed at the proximal end of the retractable deployment sheath, the sheath hub configured for actuation and manipulation of said sheath;
a system-side connector configured to mate with the catheter hub to form a hub assembly and provide fluid and electronic communication with the dialysis catheter;
a dialyzer communicating with the blood removal and return lumens through the hub assembly and at least one pressure gauge and pump to control blood flow through the dialyzer; and
at least one processor and memory containing instructions for control of the dialyzer based on signals from the sensor received through the sensing pathway and hub assembly indicative of patient fluid volume state, and wherein the at least one processor communicates with the at least one pressure gauge and pump to control a rate of dialysis treatment delivered by the system.

\* \* \* \* \*